US010597702B2

(12) United States Patent
Morin

(10) Patent No.: US 10,597,702 B2
(45) Date of Patent: Mar. 24, 2020

(54) MOLECULE DETECTION USING BORONIC ACID SUBSTITUTED PROBES

(71) Applicant: Ontera Inc., Santa Cruz, CA (US)

(72) Inventor: Trevor J. Morin, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 704 days.

(21) Appl. No.: 14/912,884

(22) PCT Filed: Aug. 26, 2014

(86) PCT No.: PCT/US2014/052765
§ 371 (c)(1),
(2) Date: Feb. 18, 2016

(87) PCT Pub. No.: WO2015/031399
PCT Pub. Date: Mar. 5, 2015

(65) Prior Publication Data
US 2016/0200773 A1 Jul. 14, 2016

Related U.S. Application Data

(60) Provisional application No. 61/870,160, filed on Aug. 26, 2013.

(51) Int. Cl.
*C12Q 1/68* (2018.01)
*C12Q 1/6818* (2018.01)
(Continued)

(52) U.S. Cl.
CPC .......... *C12Q 1/6818* (2013.01); *C07K 14/003* (2013.01); *G01N 33/533* (2013.01)

(58) Field of Classification Search
CPC .................................................. C12Q 1/6818
(Continued)

(56) References Cited

U.S. PATENT DOCUMENTS

2005/0026202 A1 2/2005 Edman et al.
2009/0142748 A1 6/2009 Smith et al.
(Continued)

FOREIGN PATENT DOCUMENTS

EP 2 230 312 A1 9/2010
WO WO 2003/044482 A2 5/2003
(Continued)

OTHER PUBLICATIONS

Debaene, F., et al: "Expanding the scope of PNA-encoded libraries: divergent synthesis of libraries targeting cysteine, serine and metalloproteases as well as tyrosine phosphatases", Tetrahedron, Elsevier Science Publishers, Amsterdam, NL, vol. 63, No. 28, Jul. 9, 2007 (Jul. 9, 2007), pp. 6577-6586.
(Continued)

*Primary Examiner* — Jezia Riley
(74) *Attorney, Agent, or Firm* — Fenwick & West LLP

(57) ABSTRACT

Provided are polymeric scaffold compositions and methods for detecting or quantitating diols such as carbohydrates or carbohydrate containing molecules (e.g., glycosylated protein). Provided herein are capture probes configured to bind to a scaffold. Also provided herein are capture probes linked to one or more reactive organoboronic moiety for binding diol-containing compounds in a solution. Methods of detecting complexes comprising diol-containing compounds for detecting or quantifying the presence of diol-containing compounds in solution using a nanopore device are also provided herein.

15 Claims, 19 Drawing Sheets

Specification includes a Sequence Listing.

(51) Int. Cl.
    C07K 14/00     (2006.01)
    G01N 33/533    (2006.01)
(58) Field of Classification Search
    USPC .......................................................... 435/6.1
    See application file for complete search history.

(56)              References Cited

U.S. PATENT DOCUMENTS

| 2009/0148887 | A1  | 6/2009  | Brustad et al. |
|---|---|---|---|
| 2011/0059447 | A1  | 3/2011  | Liew |
| 2011/0256157 | A1  | 10/2011 | Howard et al. |
| 2012/0222958 | A1* | 9/2012  | Pourmand ............... B01L 3/021 204/451 |
| 2013/0233709 | A1  | 9/2013  | Dunbar et al. |
| 2018/0155768 | A1  | 6/2018  | Cohen et al. |

FOREIGN PATENT DOCUMENTS

| WO | WO 2013012881 A2 | 1/2013 |
|---|---|---|
| WO | WO 2018/093976 A1 | 5/2018 |

OTHER PUBLICATIONS

Hargrove, A., et al: "Chemical Functionalization of Oligodeoxynucleotides with Multiple Boronic Acids for the Polyvalent Binding of Saccharides", Bioconjugate Chemistry, vol. 22, No. 3, Mar. 16, 2011 (Mar. 16, 2011), pp. 388-396.
Mader, H., et al: 11 Boronic acid based probes for microdetermination of saccharides and glycosylated biomolecules, Microchimica ACTA; An International Journal on Micro and Traceanalysis, Springer-Verlag, VI, vol. 162, No. 1-2, Mar. 17, 2008 (Mar. 17, 2008), pp. 1-34.
Martin, A., et al: Boron and nucleic acid chemistries: merging the best of both worlds, Chemical Society Reviews., vol. 42, No. 13, Jan. 1, 2013 (Jan. 1, 2013), p. 5684.
Wu, X., et al: "A 2?:?2 stilbeneboronic acid-[gamma]-cyclodextrin fluorescent ensemble highly selective for glucose in aqueous solutions", Chemical Communications—Chemcom., vol. 48, No. 36, Jan. 1, 2012 (Jan. 1, 2012), p. 4362.
Melicher, M., et al: A [beta]-Boronopeptide Bundle of Known Structure as a Vehicle for Polyol Recognition, Organic Letters, vol. 15, No. 19, Sep. 13, 2013 (Sep. 13, 2013), pp. 5048-5051.
Extended European Search Report for European Patent Application No. EP 14838934.9, dated Mar. 20, 2017, 7 Pages.
Edwards, N., et al., "Boronic Acid Based Peptidic Receptors for Pattern-Based Saccharide Sensing in Neutral Aqueous Media, an Application in Real-Life Samples," J. AM. CHEM. SOC., 2007, pp. 13575-13583, vol. 129.
Goudgaon, N., et al., "Boron Containing Pyrimidines, Nucleosides, and Oligonucleotides for Neutron Capture Therapy," Nucleosides and Nucleotides, 1994, pp. 849-880, vol. 13, No. 1-3.
Haque, et al., "Solid-State and Biological Nanopore for Real-Time Sensing of Single Chemical and Sequencing of DNA," Nano Today, 2013, 8, pp. 56-74.
Howorka, et al., "Nanopore Analytics: Sensing of Single Molecules," Chem. Soc. Rev., 2009, 38, pp. 2360-2384.
Miles, et al., "Single Molecule Sensing With Solid-State Nanopores: Novel Materials, Methods, and Applications," Chem Soc Rev, 2013, 42(15), pp. 1-15.

Plesa, C., et al., "Fast Translocation of Proteins through Solid State Nanopores," Nano Letters, 2013, pp. 658-663, vol. 13, No. 2, American Chemical Society.
Reiner, et al., "Disease Detection and Management via Single Nanopore-Based Sensors," Chemical Reviews, 2012, 112, pp. 6431-6451.
Roberts, M., et al., "Dynamically Restructuring Hydrogel Networks Formed with Reversible Covalent Crosslinks," Advanced Materials, 2007, pp. 2503-2507, vol. 19.
Schinazi, R., et al., "Synthesis of 5-(Dihydroxyboryl)-2'-deoxyuridine and Related Boron-Containing Pyrimidines," J. ORG. CHEM., 1985, pp. 841-847, vol. 50, No. 6.
Song, Y.-L., et al., "Cedranediolborane as a Borylating Agent for the Preparation of Boronic Acids: Synthesis of a Boronated Nucleoside Analogue," Synlett, 2001, pp. 266-268, No. 2.
Singer, et al., "Nanopore Based Sequence Specific Detection of Duplex DNA for Genomic Profiling," Nano Lett., 2010, 10, pp. 738-742.
Sun, W., et al., "A Fluorescent Polymeric Heparin Sensor," Chemistry a European Journal, 2007, pp. 7701-7707, vol. 13.
Tjarks, W., "The use of boron clusters in the rational design of boronated nucleosides for neutron capture therapy of cancer," Journal of Organometallic Chemistry, 2000, pp. 614-615, vol. 37-47.
Yamamoto, Y., Molecular design and synthesis of B-10 carriers for neutron captures therapy, Pure & Appl. Chem., 1991, pp. 423-426, vol. 63, No. 3.
International Preliminary Report on Patentability for PCT/US2014/036861, dated Sep. 2, 2015, 8 Pages.
International Search Report and Written Opinion for International Application No. PCT/US2014/036861, dated Sep. 18, 2014, 12 pages.
PCT Written Opinion of the International Preliminary Examining Authority for PCT/US2014/036861, dated Apr. 15, 2015, 7 Pages.
PCT International Search Report and Written Opinion for PCT/US2014/046397, dated Feb. 2, 2015, 11 Pages.
Bezrukov S. M. et al: "Counting Polymers Moving Through a Single Ion Channel", Nature, Jul. 28, 1994, pp. 279-281, vol. 370, Nature Publishing Group, United Kingdom.
Kasianowicz J. et al: "Simultaneous Multianalyte Detection with a Nanometer-Scale Pore", Analytical Chemistry, May 15, 2001, pp. 2268-2272, vol. 73(10).
Niemeyer C M: "The developments of semisynthetic DNA-protein conjugates", Trends in Biotechnology, Sep. 2002, pp. 395-401, vol. 20(9), Elsevier Publications, Cambridge, GB.
Wanunu M. et al: "DNA Profiling Using Solid-State Nanopores: Detection of DNA-Binding Molecules", Nano Letters, Oct. 14, 2009, pp. 3498-3502, vol. 9 (10).
Winters-Hilt S. "Nanopore Detector based analysis of single-molecule conformational kinetics and binding interactions", Sep. 26, 2006, pp. 1-27, vol. 7(2), BMC Bioinformatics, Biomed Central, London, GB.
Office Action for U.S. Appl. No. 14/270,283, dated Dec. 11, 2015, 6 Pages.
Communication pursuant to Article 94(3) EPC for European Patent Application No. EP 14733761.2, dated Jan. 17, 2017, 3 Pages.
Patent Cooperation Treaty, International Search Report and Written Opinion of the International Searching Authority, International Patent Application No. PCT/US2014/052765, dated Dec. 30, 2014, 19 Pages.

* cited by examiner

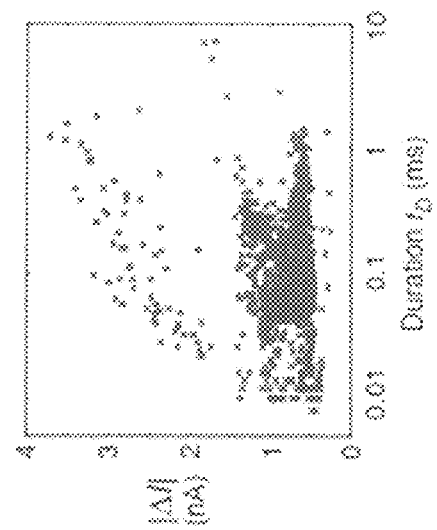
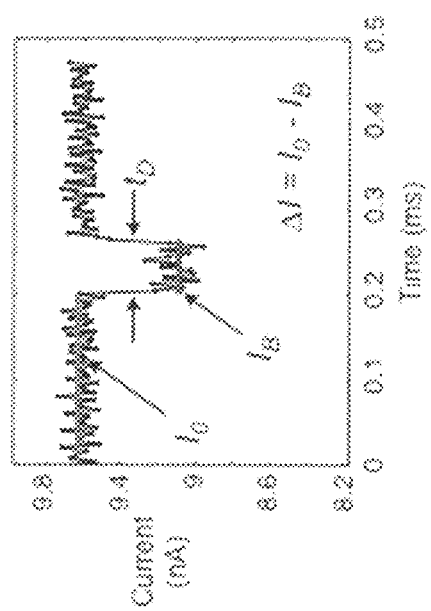
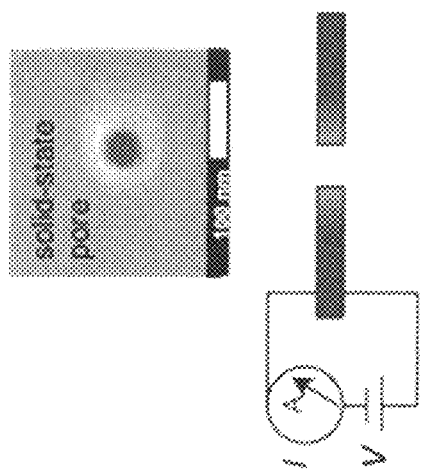
FIG. 9a
FIG. 9b
FIG. 9c

1. Ladder
2. 15x PNA to binding sites
3. 25x PNA to binding sites
4. DNA only
5. 30x PNA to binding sites
6. 40x PNA to binding sites
7. DNA only
8. 50x PNA to binding sites

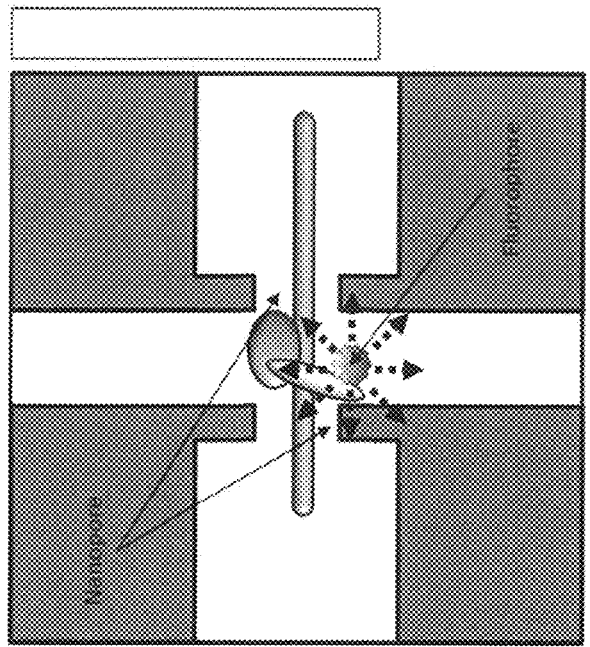
FIG. 15b Top View of Nanopore Device
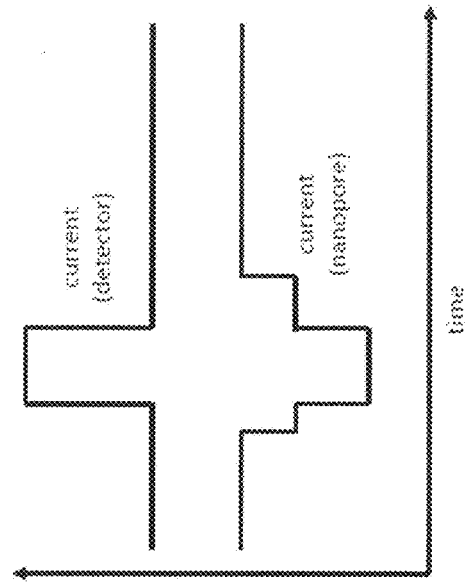
FIG. 15c Fluorescence vs Nanopore Data
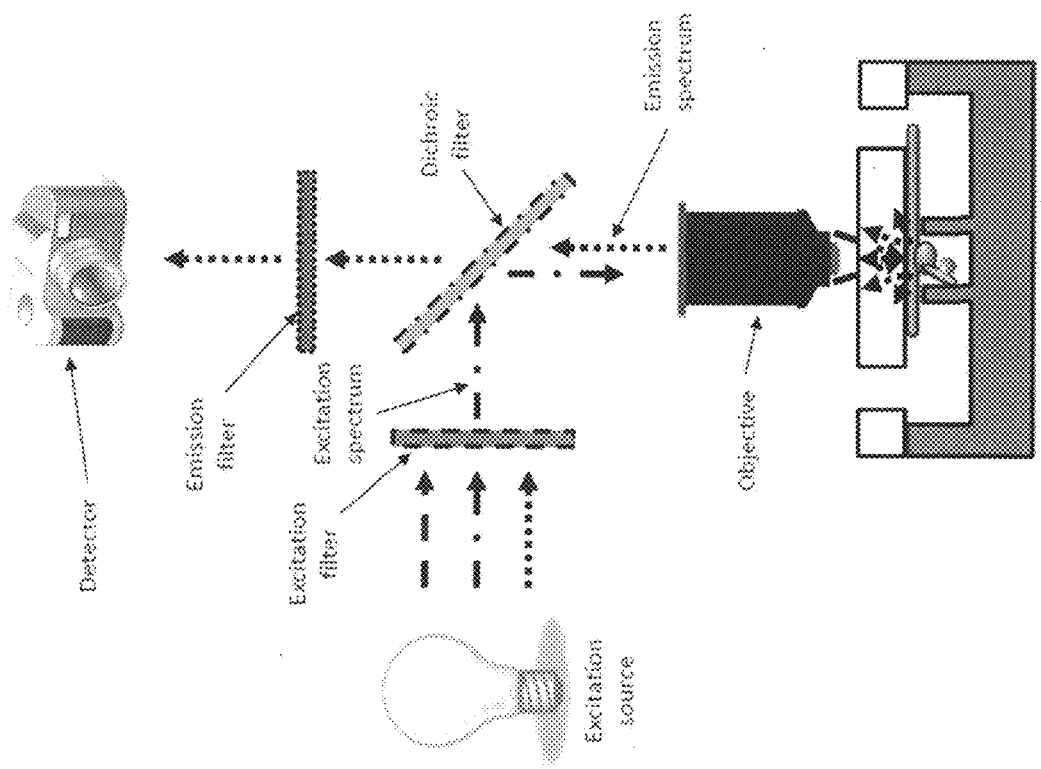
FIG. 15a Fluorophore Enhanced Nanopore

MOLECULE DETECTION USING BORONIC ACID SUBSTITUTED PROBES

CROSS-REFERENCE TO RELATED APPLICATION

This application is the National Stage of International Application No. PCT/US14/52765, which claims the benefit of U.S. Provisional Patent Application No. 61/870,160, filed Aug. 26, 2013, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Oct. 14, 2014, is named 27560PCT_CRF_sequencelisting.txt and is 534 bytes in size.

BACKGROUND

Molecular detection and quantitation can be carried out with various methods depending on the type of the molecule. For instance, nucleotide sequences can be detected by virtue of their sequence complementarily to a probe or primer, or in fewer occasions with a protein that recognize the sequence. A protein is commonly detected with an antibody that specifically recognizes and binds the protein, as in enzyme-linked immunosorbent assay (ELISA) or Western Blot assay. Molecular detection methods and systems have broad applications, in particular clinically, for detection that can give a disease diagnosis, for instance.

Detecting small molecules, for example mono- and disaccharides, or larger molecules, like proteins that are shielded with glycosylation, presents a challenge. Unlike nucleic acids, they do not have a complementary sequence, and unlike proteins, they lack a unique targetable sequence. Thus, their structures makes it difficult to generate highly-specific, high-affinity antibodies to detect their presence.

Diol compounds alone, below a certain size threshold, are undetectable with a nanopore, as exemplified by Calin Plesa, Stefan W. Kowalczyk, Ruben Zinsmeester, Alexander Y. Grosberg, Yitzhak Rabin, and Cees Dekker. "Fast translocation of proteins through solid state nanopores." Nano letters 13, no. 2 (2013): 658-663. Moreover, even those diol-containing molecules that are detectable may not be distinguishable. A diol compound will yield the same nanopore signature as all other molecules of comparable size/charge, preventing discrimination.

What is needed therefore, is a fast and inexpensive method of detecting, distinguishing and quantifying small molecules and metabolites, or larger proteins with small molecule post translational modifications. These biomolecules may serve as biomarkers for the presence of disease.

SUMMARY

Provided are devices, compositions and methods for the detection or quantitation of target molecules, in particular, those containing diols, e.g., mono- or disaccharide, glycans, or glycan-containing proteins. The technology entails the use of a capture molecule that includes a nucleic acid, polypeptide, or PNA (Protein Nucleic Acid) probe linked to one or more reactive organoboronic moiety. The reactive organoboronic moiety is capable of specifically recognizing and binding a diol and the probe can specifically recognize and bind a motif on a polymer scaffold. When the polymer scaffold is passed through a nanopore device, the binding status of the motif, that is whether it is bound by a capture molecule only, or a capture molecule that is also bound to a diol containing molecule, can be determined.

In an embodiment, provided herein is a composition comprising a probe, wherein the probe comprises an organoboronic moiety, and wherein the probe is configured to bind to a polymeric scaffold. In an embodiment, the probe comprises a nucleic acid, polypeptide, or PNA.

In an embodiment, the probe comprises a polynucleotide. In an embodiment, the polynucleotide is not longer than 100 bases in length. In some embodiments, the organoboronic moiety is covalently linked to the backbone of the polynucleotide. In other embodiments, the organoboronic moiety is covalently linked to a base in the polynucleotide.

In an embodiment, the probe comprises a peptide nucleic acid (PNA). In a further embodiment, the peptide nucleic acid is not longer than 100 bases in length. In certain embodiments, the organoboronic moiety is covalently linked to the nucleic acid at the backbone of the peptide nucleic acid. In other embodiments, the organoboronic moiety is covalently linked to the nucleic acid at a base in the peptide nucleic acid.

In some embodiments, the organoboronic moiety is bound to a linker, and wherein the linker is bound to the probe. In some embodiments, the linker comprises an amino acid. In certain embodiments, the linker is:

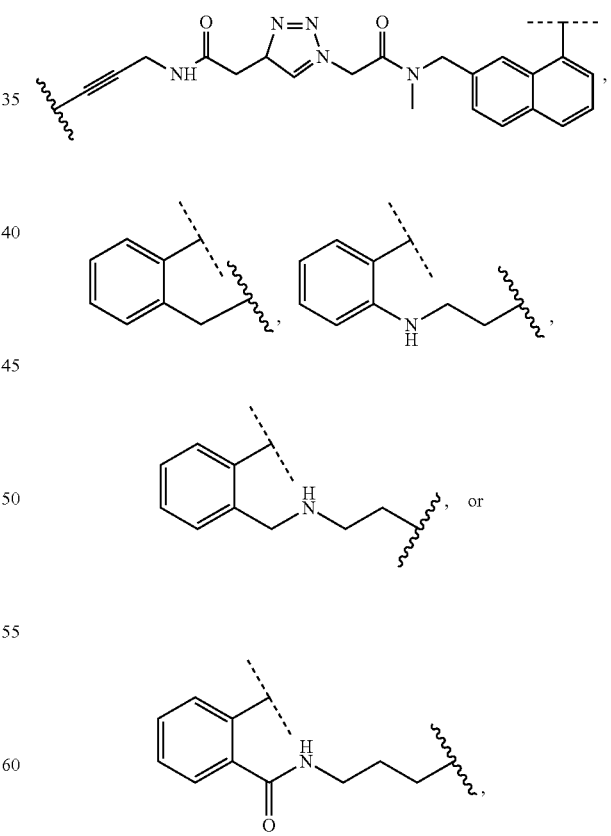

wherein ----- represents the point of connection or linkage of the reactive organoboronic moiety to the linker and represents the point of connection or linkage to the probe.

In other embodiments, the linker is:

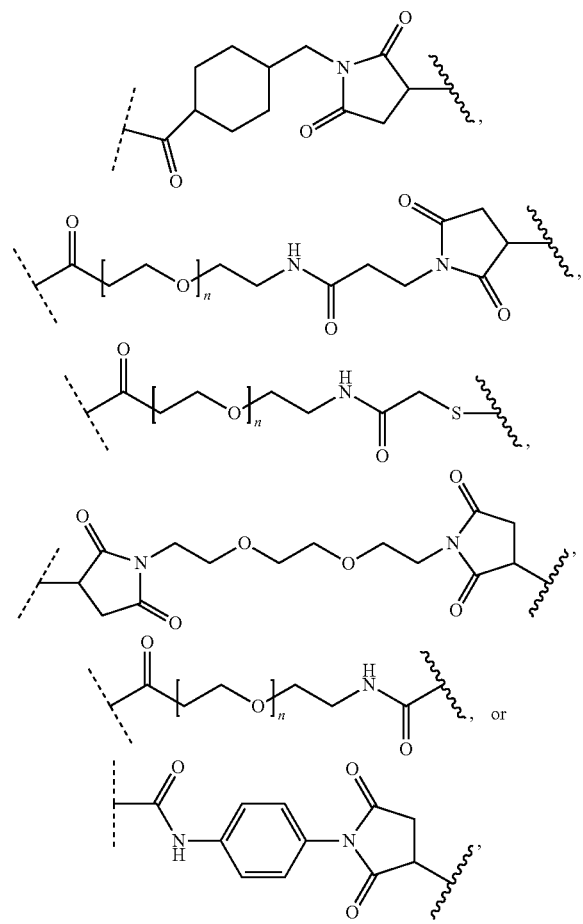

wherein ----- represents the point of connection or linkage of the reactive organoboronic moiety to the linker and ∿∿∿ represents the point of connection or linkage to the PNA.

In some embodiments, the probe comprises a polypeptide. In certain embodiments, the polypeptide comprises a binding domain selected from the group consisting of: a helix-turn-helix, a zinc finger, a leucine zipper, a winged helix, a winged helix turn helix, a helix-loop-helix and an HMG-box.

In an embodiment, the polymeric scaffold comprises a polynucleotide. In some embodiments, the polymeric scaffold is single-stranded. In other embodiments, the polymeric scaffold is double-stranded. In selected embodiments, the polymeric scaffold is at least 100 bases in length. In some embodiments, the probe is configured to bind to at least 2, 3, 4, 5, 6, 7, 8, 9, 10, 11, 12, 13, 14, 15, 16, 17, 18, 19, or 20 consecutive bases of the polynucleotide.

In some embodiments, the organoboronic moiety is capable of binding to a diol or diol containing molecule or compound. In a further embodiment, the diol is an α,β-diol. In certain embodiments, the organoboronic moiety is selected from the group consisting of: boronic acid, boronic acid derivative, activated boronic ester, and boronic ester derivative.

In some embodiments, the probe is configured to bind at a binding site on the polymeric scaffold, wherein the binding site has sequence complementarity with an oligomer or polynucleotide sequence on the probe. In certain embodiments, the probe is bound to the binding site of the polymeric scaffold. In some embodiments, the organoboronic moiety is bound to a diol or diol-containing compound.

Also provided herein is a composition comprising a polymeric scaffold bound to a probe, wherein the probe is covalently linked to one or more reactive organoboronic moiety.

Also provided herein is a composition comprising a first probe covalently linked to a first organoboronic moiety, wherein the first organoboronic moiety is capable of binding to a first diol, and wherein the composition further comprises a second probe covalently linked to a second organoboronic moiety capable of binding to a second diol, wherein the first and second diol are different, and wherein the first and second organoboronic moieties are different. In an embodiment, the first probe comprises a region complementary to a first sequence on a polymeric scaffold, and wherein the second probe comprises a region complementary to a second sequence on a polymeric scaffold, wherein the first and second sequence are different.

Also provided herein is a method for detecting a diol suspected to be present in a sample, the method comprising: contacting the sample with a nucleic acid or polypeptide probe covalently linked to one or more reactive organoboronic moiety that is capable of specifically binding to the diol under conditions for the diol to bind to the reactive organoboronic moiety; loading a polymeric scaffold, in the presence of the sample, through a pore of a device, wherein the pore is located between two volumes of an interior space of the device, wherein the device is configured to pass the polymeric scaffold through the pore from one volume to the other volume, wherein the device further comprises a sensor configured to identify objects passing through the pore, and wherein the probe specifically recognizes and binds to a site on the polymeric scaffold; and determining with the sensor whether the probe bound to the polynucleotide is bound to the diol.

In an embodiment, the sample is contacted with a plurality of probes, each linked to a reactive organoboronic moiety capable of specifically binding to different diols, and wherein the polymeric scaffold comprises binding sites that can be specifically bound by each of the probes. In another embodiment, the method further comprises applying a condition suspected to alter the binding interaction between the reactive organoboronic moiety and a corresponding diol and repeating the step of determining whether the probe bound to the polynucleotide is bound to the diol. In some embodiments, the condition suspected to alter the binding interaction is pH, salt, temperature, or addition or removal of an inhibitor Also provided herein is a composition comprising a peptide nucleic acid (PNA) covalently linked to one or more reactive organoboronic moiety, wherein the PNA is not longer than 100 bases in length. In an embodiment, the reactive organoboronic moiety is covalently linked to the PNA at the backbone of the PNA.

In some embodiments, the reactive organoboronic moiety is covalently linked to the PNA at one or more nucleic acid bases of the PNA. In some embodiments, the reactive organoboronic moiety is covalently linked to the PNA through a linker. In an embodiment, the linker is a compound disclosed herein. In some embodiments, the reactive organoboronic moiety is capable of binding to a diol.

An embodiment provides a polymeric scaffold, such as double stranded DNA, being bound by a nucleic acid, polypeptide, or PNA probe which is covalently linked to one or more reactive organoboronic moieties. In some embodiments, the reactive organoboronic moiety is itself bound to a diol, such as an α,β-diol.

An embodiment provides a composition comprising (a) a polymeric scaffold and (b) a nucleic acid, polypeptide, or PNA probe covalently linked to one or more reactive organoboronic moiety, wherein the probe is capable to specifically recognizing and bind to a fragment of the polynucleotide. In some aspects, the probe is a nucleic acid. In some aspects, the probe is a peptide nucleic acid (PNA). In some aspects the probe binds to a unique site in the polymer, e.g. based on polymer sequence. In some aspects the probe is not specific, but can bind non-specifically to the scaffold. In some aspects the probe is not longer than 100 bases in length.

In some aspects, the reactive organoboronic moiety is covalently linked to the probe at the backbone of the probe. In some aspects, the reactive organoboronic moiety is covalently linked to the probe at a base of the probe.

In some aspects, the reactive organoboronic moiety is covalently directly linked to the probe. In some aspects, the reactive organoboronic moiety is covalently attached through a linker. In some aspects, the linker comprises an amino acid, peptide, nucleotide, polynucleic acid, carbon chain, PEG chain.

In some aspects, the linker is a divalent group containing 1 to 40 carbon atoms and optionally 1 to 10 heteroatoms selected from the group consisting of oxygen, NR', sulfur and —SO2— where R' is hydrogen or C1 to C10 alkyl. In an embodiment, the linker is selected from a group consisting of:

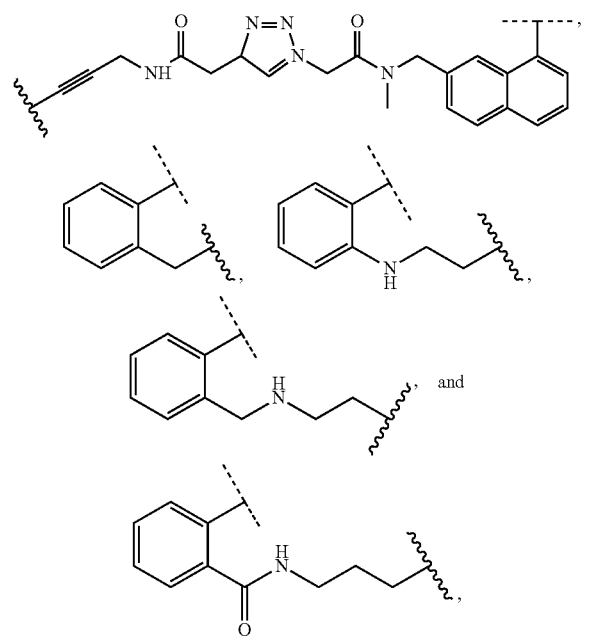

wherein ---- represents the point of connection or linkage of the reactive organoboronic moiety to the linker and ∿∿∿ represents the point of connection or linkage to the probe.

In some aspects the linkage is through esters that react with primary amines. In some aspects the linkage is through thiols or maleimides that react with thiolates. In some aspects the linkage is through hydroxyls and isocyanates.

Example linkers for this chemistry are show below. ---- represent the point of connection to the organoboronic moiety and ∿∿∿ represent the point of connection to the probe:

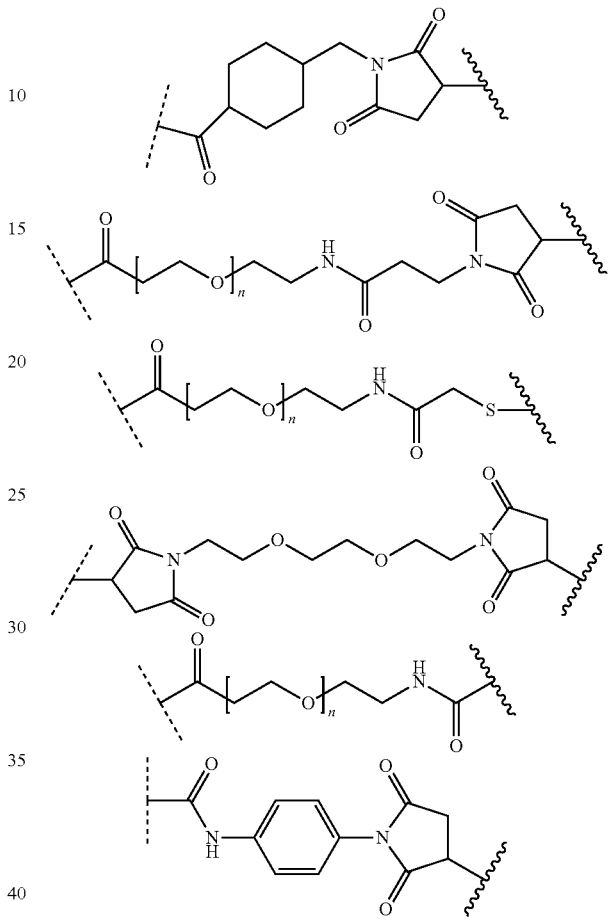

Examples of organoboronic derivatives compatible with the above linkers have the following structures:

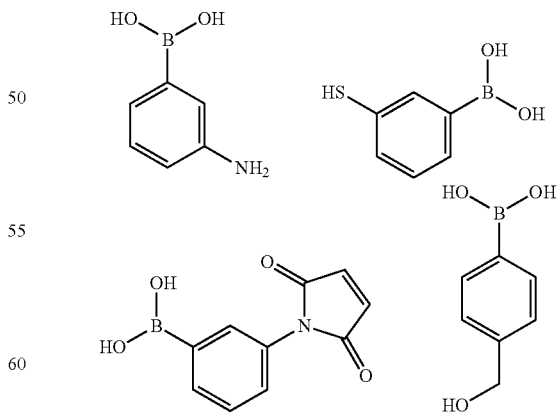

In some aspects, the binding site has sequence complementarily with the probe.

In some aspects, the probe is a polypeptide probe. In some aspects, the polypeptide probe comprises a binding domain selected from the group consisting of a helix-turn-helix, a zinc finger, a leucine zipper, a winged helix, a winged helix turn helix, a helix-loop-helix and an HMG-box.

In some aspects, the probe is a PNA, LNA, TALEN, CRISPR, is an aptamer, oligonucleotide, In some aspects, the reactive organoboronic moiety is capable of binding to a diol. In some aspects, the diol is a carbohydrate. In some aspects, the reactive organoboronic moiety is selected from the group consisting of boronic acid, boronic acid derivative, activated boronic ester, boronic ester derivative, phenyl boronic acid, and phenyl boronic acid derivative, for example maleimido, hydroxyl, amino, carboxylate, and mercapto. The boronic acid moiety is linked to the probe, typically through a covalent bond. The formation of such a covalent linkage is performed by using conventional reactive complementary functionalities. That is to say that the reactive functionality on the organoboronic moiety is capable of reacting with (or can be modified to react with) a reactive functionality on the probe under conditions well known in the art to form a covalent bond. Examples of complementary reactive functionalities are found in the Table below:

| Reactive group on boronic acid derivative | Linker reactivity to boronic acid derivative | Linker reactivity to probe | Reactive group on probe |
| --- | --- | --- | --- |
| Alcohol | Isocyanate | Maleimide | thiolate |
| Amine | Activated ester | Maleimide | thiolate |
| Amine | Activated ester | pyridyl | thiolate |
| Thiol | Maleimide | Maleimide | Thiolate |
| Maleimide | | | thiolate |
| Amine | Activated ester | Activated ester | Amine |
| Thiol | Maleimide | Activated ester | Amine |
| Alcohol | Isocyanate | Activated ester | amine |
| Carboxylate | Amide | Carboxylate | amine |

In some aspects, the scaffold is single-stranded polynucleotide. In some aspects, the scaffold is double-stranded polynucleotide. In some aspects, the scaffold is at least about 100 bases in length. In some aspects, the probe is bound to a fragment of the polynucleotide.

In some aspects, the composition further comprises one or more different probes, wherein each probe is covalently linked to one or more reactive organoboronic moiety and the probe has specificity to different sites on the scaffold. In some aspects, the reactive organoboronic moiety of each of the probes has specificity to different diols.

Another embodiment provides a method for detecting a diol suspected to be present in a sample, comprising: a) contacting the sample with a probe covalently linked to one or more reactive organoboronic moiety that is capable of specifically binding to the diol, under conditions for the diol to bind to the reactive organoboronic moiety; b) loading a scaffold, in the presence of the sample, through a pore of a device comprising the pore that separates an interior space of the device into two volumes, and configuring the device to pass the scaffold through the pore from one volume to the other volume, wherein the device further comprises a sensor (either the pore itself or adjacent to the pore) configured to identify objects passing through the pore, and wherein the probe specifically recognizes and binds to a location on the scaffold; and c) determining with the sensor, whether the probe bound to the polynucleotide is bound to the diol. In some aspects, step (a) is performed prior to step (b). In some aspects, step (b) is performed prior to step (a).

In some aspects, the sample is contacted with more than one probes each linked to a reactive organoboronic moiety capable to specifically bind to different diols, and wherein the scaffold comprises binding sites that can be specifically bound by each of the probes.

In some aspects, the method further comprises applying a condition suspected to alter the binding between the reactive organoboronic moiety and a corresponding diol and carrying out step c) again. In some aspects, the condition is selected from the group consisting of pH, salt and temperature, or adding a (competitive) inhibitor Yet another embodiment provides a molecule comprising a peptide nucleic acid (PNA) covalently to one or more reactive organoboronic moiety, wherein the PNA is not longer than 100 bases in length. In some aspects, the reactive organoboronic moiety is covalently linked to the PNA at the backbone of the PNA. In some aspects, the reactive organoboronic moiety is covalently linked to the PNA at a DNA base of the PNA.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

Specifically, FIG. 8a is a schematic of a dual-pore chip and a dual-amplifier electronics configuration for independent voltage control (V1, V2) and current measurement (I1, I2) of each pore. Three chambers, A-C, are shown and are volumetrically separated except by common pores. Feasible chip parameters are, for example, an inter-pore distance 10-500 nm, membrane thickness 0.3-50 nm, and pore diameters 1-100 nm.

FIG. 8b is a schematic where electrically, V1 and V2 can principally cross each nanopore resistance, by constructing a device that minimizes all access resistances to effectively decouple I1 and I2.

In FIG. 8c, competing voltages are used for control, with blue arrows showing the direction of each voltage force. Assuming pores with identical voltage-force influence and using $|V1|=|V2|+\delta V$, the value $\delta V>0$ (<0) is adjusted for tunable motion in the V1 (V2) direction. In practice, although the voltage-induced force at each pore will not be identical with V1=V2, calibration experiments can identify the required voltage bias that will result in equal pulling forces, for a given two-pore chip, and variations around that bias can then be used for directional control.

FIG. 9 illustrates a solid-state pore and analysis of molecules captured in the nanopore via current signature. FIG. 9a illustrates a solid-state nanopore. FIG. 9b shows the current signature that results when a molecule passes through a nanopore, giving a representative dwell time $t_D$ and change in current amplitude $\Delta I$. FIG. 9(c) shows a plot of dwell time vs. change in current amplitude for multiple events, which allows visualization of distinct populations of molecules that pass through the nanopore.

FIG. 15a is a schematic of a system that combines a nanopore device with an epifluorescence microscope to enable detection of a compound comprising a fluorophore. FIG. 15b illustrates an excited fluorophore that is detected by an epifluorescence microscope as the fluorophore passes through an in-plane two nanopore device. FIG. 15c shows the change in the current amplitude and the corresponding fluorescent signal when a scaffold bound to a fluorophore passes through the nanopore

DETAILED DESCRIPTION

Figure 1:
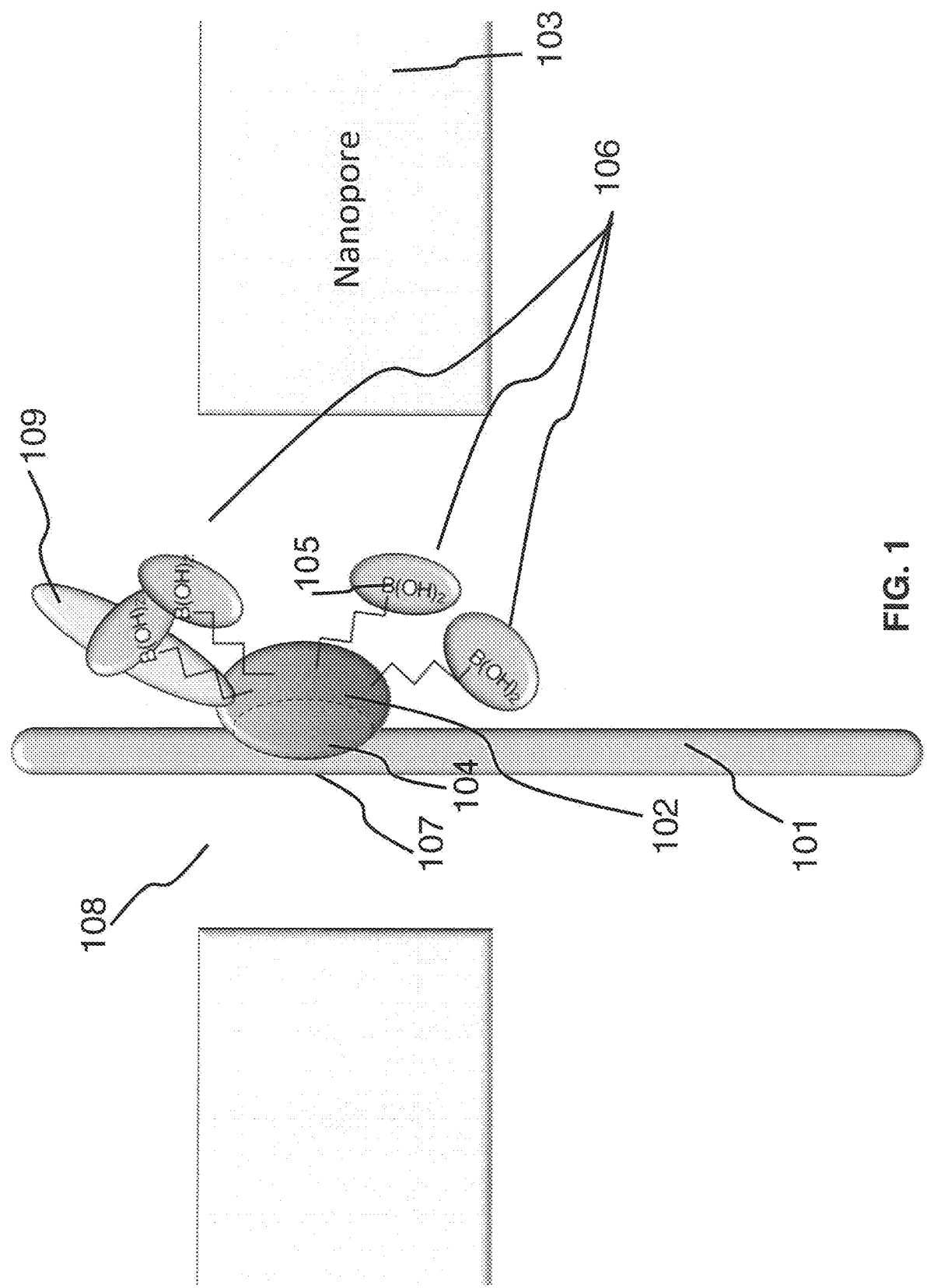
FIG. 1 illustrates capture and detection of a target molecule in a nanopore with an embodiment of the presently disclosed method.

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a," "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

The term "diol" refers to a compound having at least 2 hydroxy groups (—OH) bound to the molecule in an orientation which permits the diol to bind to the boron of the organoboronic acid moiety. In some aspects, at least 2 of the hydroxy groups are on adjacent carbon atoms and such a conformation is sometimes referred to as an $\alpha,\beta$-diol or a 1,2-diol. In some embodiments, at least two of the hydroxyl groups are on carbon atoms separated by a single carbon atom. In such cases, the compound is referred to as a 1,3-diol. It is understood that a compound can have more than 1 diol which is capable of binding to the boron.

As to the term "compound," it refers a compound of from 2 to about 100 carbon atoms having at least one diol which is capable of binding to the boron of the organoboronic group. The binding may be covalent, ionic or chelating. Examples of such compounds include ethylene glycol ($HOCH_2CH_2OH$), catechol, and simple to complex sugars/carbohydrates. Complex carbohydrates include oligosaccharides of up to 12 saccharide (sugar) units. The saccharides can include functionality other than hydroxyl groups including for example, glucosamine, N-acetylglucosamine, sialic acid and the like.

A carbohydrate is an organic compound comprising only carbon, hydrogen, and oxygen, usually with a hydrogen:oxygen atom ratio of 2:1 (as in water); in other words, with the empirical formula $Cm(H2O)n$ (where m could be different from n). Natural simple carbohydrates are referred to as monosaccharides with general formula $(CH2O)n$ where n is three or more. Examples of monosaccharides are glucose, fructose, and glyceraldehydes.

Two joined monosaccharides are called a disaccharide and these are the simplest polysaccharides. Examples include sucrose and lactose. They are composed of two monosaccharide units bound together by a covalent bond known as a glycosidic linkage formed via a dehydration reaction, resulting in the loss of a hydrogen atom from one monosaccharide and a hydroxyl group from the other. The formula of unmodified disaccharides is $C_{12}H_{22}O_{11}$.

The term "oligosaccharide" refers to a carbohydrate structure having from 2 to about 7 saccharide units (disaccharides, trisaccharides, etc.). The particular saccharide units employed are not critical, and include by way of example, all natural and synthetic derivatives of glucose. In addition to being in their pyranose form, all saccharide units within the scope of this disclosure can be in their D form, or, like fucose which is in its L-form.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary and that equivalents of such are known in the art.

The term "nanopore" (or, just "pore") as used herein refers to a single nano-scale opening in a membrane that separates two volumes. The pore can be a protein channel inserted in a lipid bilayer membrane, for example, or can be engineered by drilling or etching or using a voltage-pulse method through a thin solid-state substrate, such as silicon nitride or silicon dioxide or graphene or layers of combinations of these or other materials. Geometrically, the pore has dimensions no smaller than 0.1 nm in diameter and no bigger than 1 micron in diameter; the length of the pore is governed by the membrane thickness, which can be sub-nanometer thickness, or up to 1 micron or more in thickness. For membranes thicker than a few hundred nanometers, the nanopore may be referred to as a "nano channel."

As used here, the term "nanopore instruments" refers to devices that combine the nanopore with circuitry for sensing single molecule events. Specifically, nanopore instruments use a sensitive voltage-clamp amplifier to apply a voltage across the pore while measuring the ionic current through the open pore. When a single charged molecule such as a double-stranded DNA (dsDNA) is captured and driven through the pore by electrophoresis, the measured current shifts, indicating a capture event (i.e., the translocation of a molecule through the nanopore, or the capture of a molecule in the nanopore), and the shift amount (in current amplitude) and duration of the event are used to characterize the molecule captured in the nanopore. After recording many events during an experiment, distributions of the events are analyzed to characterize the corresponding molecule according to its shift amount (i.e., its current signature). In this way, nanopores provide a simple, label-free, purely electrical single-molecule method for biomolecular sensing.

Molecular Detection

The present disclosure provides methods and systems for molecular detection and quantitation, in particular for diols such as carbohydrates and for molecules that have carbohydrates attached, e.g. glycosylated protein. In addition, the methods and systems can be configured to measure the affinity of molecule binding. Further, such detection, quantitation, and measurement can be carried out in a multiplexed manner, greatly increasing its efficiency.

FIG. 1 provides an illustration of an embodiment of a system of the present technology. More specifically, the system includes a polymer scaffold 101, a capture molecule 102 and a nanopore device 103. Further, the capture molecule (102) includes a nucleic acid, polypeptide, or PNA probe 104 (or simply "probe") to which a reactive organoboronic moiety 105 attached. It is contemplated that the reactive organoboronic moiety can be attached to the probe by any means including but not limited to covalent bond, a hydrogen bond, an ionic bond, a metallic bond, van der Waals force, hydrophobic interaction, or planar stacking interaction. In some embodiments, the reactive organoboronic moiety is covalently attached to the probe.

The reactive organoboronic moiety is capable of binding to a target molecule 106 desired to be detected or quantitated. Meanwhile, the probe is capable of binding to a specific binding motif 107 on the polymer scaffold.

Therefore, if all present in a solution, the capture molecule 102 binds, on the one end, to the polymer scaffold 101 (or simply "polymer") through the specific recognition and binding between the binding motif 107 and the probe 104, and on the other end, to the target molecule by virtue of the interaction between the reactive organoboronic moiety 105 and the target molecule 106. Such binding causes the formation of a complex that includes the polymer, the capture molecule and the target molecule.

The formed complex can be detected by a device (103) that includes a pore (108) that separates an interior space of the device into two volumes, and a sensor (the pore itself or adjacent to the pore) configured to identify objects passing through the pore. This device is referred throughout as a "nanopore." In some embodiments, the nanopore also includes means, such as electrodes connected to power sources, for moving the polymer from one volume to another, across the pore. As the polymer can be charged or be modified to contain charges, one example of such means generates a potential or voltage differential across the pore to facilitate and control the movement.

When a sample that includes the formed complex is loaded to the nanopore, the nanopore can be configured to pass the polymer through the pore. When the binding motif is within the pore or adjacent to the pore, the binding status of the motif can be detected by the sensor.

Figure 6:
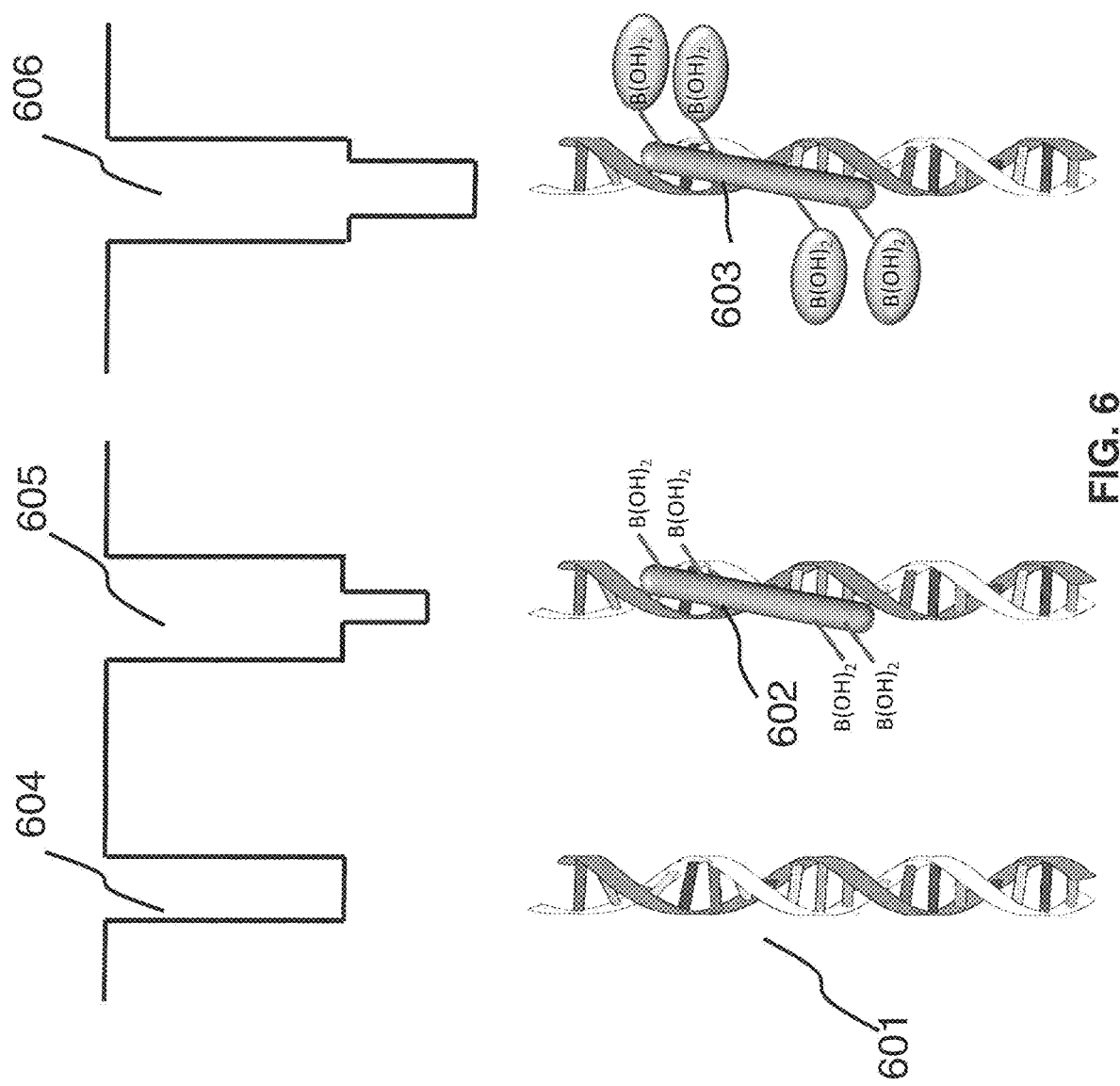
FIG. 6 shows the change in current amplitude when a scaffold passes through the nanopore when it is unbound (left), bound to a capture molecule (middle), or bound to a capture molecule that is bound to the target molecule (right), respectively.

The "binding status" of a binding motif, as used herein, refers to whether the binding motif is bound to a capture molecule with a corresponding binding domain, and whether the capture molecule is also bound to a target molecule. Essentially, the binding status can be one of three potential statuses, (i) the binding motif is free and not bound to a capture molecule (see 601 in FIG. 6), (ii) the binding motif is bound by a capture molecule that does not bind to a target molecule, (see 602 in FIG. 6), or (iii) the binding motif is bound to a capture molecule that is bound to a target molecule (see 603 in FIG. 6).

Detection of the binding status of a binding motif can be carried out by various methods. In one aspect, by virtue of the different sizes of the binding motif at each status, when the binding motif passes through the pore, the different sizes result in different currents across the pore (FIG. 6, 604 unoccupied binding site, 605 occupied by the capture molecule, 606 occupied by the capture/target complex). In this respect, no separate sensor is required for the detection, as the electrodes, which are connected to a power source and can detect the current, thus serving the sensing function. Either or both the electrodes, therefore, serve as a "sensor."

In some aspects, an agent (109-FIG. 1) can be added to the complex to aid detection. This agent is capable of binding to the target molecule or the capture/target molecule complex. In one aspect, the agent includes a charge, either negative or positive, to facilitate detection. In another aspect, the agent adds size to facilitate detection. In another aspect, the agent includes a detectable label, such as a fluorophore.

To detect a fluorophore in the nanopore, a nanopore device fabricated in-plane with a glass cover is combined with an epifluorescence microscope to enable dual current amplitude and fluorescence signal detection. FIG. 15a shows how the microscope can be used to detect a fluorophore in the nanopore device. The nanopore device is placed underneath the objective of an epifluorescence microscope. As the nanopore measurement is performed, the microscope monitors the nanopore region. The nanopore region is illuminated by means of a broadband excitation source that is filtered such that only the wavelengths corresponding to the excitation spectrum of the fluorophore are allowed to pass through. A dichroic filter selectively allows transmission of the wavelengths corresponding to the emission spectrum of the fluorophore while reflecting all other wavelengths. As the fluorophore modified binding molecule passes through the nanopores the fluorophore absorbs the excitation spectrum and reemits an emission spectrum. An emission filter in front of the detector ensure that only wavelengths corresponding to the emission spectrum of the fluorophore are detected. Thus the detector will only detect a signal when the fluorophore passes through the nanopore. FIG. 15b shows a top down view of the nanopore device as viewed by the microscope during emission of the fluorophore. FIG. 15c demonstrates how the detection of the fluorophore can be used in conjunction with the signal from the nanopore. The use of two signals enhances the confidence in the detection of the biomolecule.

In this context, an identification of status (iii) indicates that a polymer-capture molecule-target molecule complex has formed. In other words, the target molecule is detected.

The present molecules, compositions and methods can be used to detect the presence of diols. In some embodiments, the detection of diols is quantitative. For instance, if the polymer scaffold is relatively long, being able to bind to multiple (e.g., more than 10, 50, 100, 200, 500, 1000) probes. then, the ratio of the number or probes bound to the polymer being further bound by a diol over the total number of probes bound to the polymer is reflective of the concentration or amount of diols in a sample. In this respect, a standard curve for that particular condition can be established for the purpose of quantitation.

Polymer Scaffold

Non-limiting examples of polymers include nucleic acids such as deoxyribonucleic acid (DNA), ribonucleic acid (RNA), or peptide nucleic acid (PNA), and linearized proteins or peptides. A DNA or RNA can be single-stranded or double-stranded, or can be a DNA/RNA hybrid molecule. The polymer does not need to be linearized and thus could be spherical, such as a dendrimer.

In one aspect, the polymer is synthetic or chemically modified. Chemical modification can help stabilize the polymer, add charges to the polymer to increase mobility, maintain linearity, or add or modify binding specificity. In some aspects, the chemical modification is biotinylation, acetylation, methylation, summolation, oxidation, phosphorylation, glycosylation, or PEG modified.

In some aspects, the polymer is charged. DNA, RNA, and proteins are typically charged under physiological conditions. Such polymers can be further modified to increase or decrease charge. Other polymers, such as PNA, can be modified to introduce charges. Charges on the polymer can be useful for driving the polymer to pass through the pore of a nanopore device. For instance, a charged polymer can move across the pore by virtue of an application of voltage across the pore.

In some aspects, when charges are introduced to the polymer, the charges can be added at the ends of the polymer. In some aspects, the charges are spread over the polymer.

In an embodiment, each unit of the charged polymer is charged at the pH selected. In another embodiment, the charged polymer comprises sufficient charged units to be pulled into and through the pores by electrostatic forces. For example, a peptide containing sufficient entities that can be charged at a selected pH (lysine, aspartic acid, glutamic acid, histidine, etc.) so as to be used in the devices and methods described herein is a charged polymer for purposes of this invention. Likewise, a copolymer comprising methacrylic acid and ethylene is a charged polymer for the purposes of this invention. In an embodiment, the charged polymer comprises one or more charged units at or close to one terminus of the polymer. In another embodiment, the charged polymer comprises one or more charged units at or close to both termini of the polymer. One co-polymer example is DNA wrapped around a protein (e.g. DNA/nucleosome). Another example of a co-polymer is linearized protein conjugated to DNA at the N- or C-terminus.

Binding Motifs and Probes

When the polymer scaffold comprises nucleic acids or polypeptides, a binding motif can be a nucleotide(s) or peptide sequence that is recognizable by a probe, which may be a functional portion of a protein or a stretch of bases of nucleic acid (e.g. A, T, C, G, U, or modified versions thereof, e.g. J (isocytosine)).

In some embodiments, the probe is a nucleic acid probe. By virtue of the sequence complementarity, a nucleic acid probe can recognize and bind to a sequence on a polynucleotide, which serves as the polymer scaffold. In some embodiments, the nucleic acid probe can be DNA, RNA, or peptide nucleic acid (PNA), single-stranded or double-stranded. In one aspect, the nucleic acid probe is a PNA probe.

In some aspects, the modified bases are used to increase the affinity of the probe for is cognate binding site. For PNA, a G-clamp is used (see, e.g., Kuhn, Heiko, Bichismita Sahu, Srinivas Rapireddy, Danith H. Ly, and Maxim D. Frank-Kamenetskii. "Sequence specificity at targeting double-stranded DNA with a γ-PNA oligomer modified with guanidinium G-clamp nucleobases." Artificial DNA, PNA & XNA 1, no. 1 (2010): 45.), along with modifying the PNA to have terminal Lysine residue (Bentin, Thomas, H. Jakob Larsen, and Peter E. Nielsen. "Combined triplex/duplex invasion of double-stranded DNA by "tail-clamp" peptide nucleic acid." Biochemistry 42, no. 47 (2003): 13987-13995.), which also aid in binding.

In some embodiments, the nucleic acid probe is at least 2, 3, 4, 5, 6, 7, 8 9, 10, 11, 12, 13, 14, 15, 16, 17, 18, 19, 20, 21, 22, 23, 24, 25, 30, 35, 40, 45, 50, 60, 70, 80, 90 or 100 bases (or basepairs) long. In some embodiments, the nucleic acid probe is not longer than about 500, 400, 300, 200, 150, 100, 90, 80, 70, 60, 50, 40, 30, 20, 15 or 10 bases (or basepairs).

In some aspects, the binding motif includes a chemical modification that causes or facilitates recognition and binding by the binding domain on the capture molecule. For example, methylated DNA sequences can be recognized by transcription factors, DNA methyltransferases or methylation repair enzymes, or biotin to capture avidin family members, or unnatural amino acids.

Molecules, in particular proteins, that are capable of specifically recognizing nucleotide binding motifs are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences. Also, PNA molecules are capable of specifically recognizing nucleotide binding motifs, along with TALENs and CRISPRs.

Target Molecules and Reactive Organoboronic Moieties

In the present technology, a target molecule is detected or quantitated by virtue of its reacting with a reactive organoboronic moiety on the capture molecule that is capable of binding to a polymer scaffold. A target molecule and a corresponding reactive organoboronic moiety on a capture molecule, therefore, are a pair of molecules, or portions of molecules, that can recognize and bind each other.

The reactive organoboronic moiety is a chemical group that includes one or more organic boron which is capable of reacting with other molecules. Non-limiting examples of reactive organoboronic moieties include boronic acid and boronic acid derivatives (phenyl, phenyl esters, and cyclic boronic acids) that react with molecules containing diols. When such reactive organoboronic moieties are used, the system and method can be used to detect or quantitate diols, such as carbohydrates or carbohydrate containing molecules and proteins.

Depending on the group connected to the reactive organoboronic moiety, the reactive organoboronic moiety is able to specifically recognize and bind to different types of diols. In some embodiments, the diols are α,β-diols. In some embodiment, the α,β-diols can take a cis-conformation in a solution. In some embodiments, the α,β-diols are carbohydrates such as blood sugar.

Attachment of One or More Reactive Organoboronic Moieties to a Probe

In some aspects, the capture molecule is prepared by linking a reactive organoboronic moiety with a nucleic acid, polypeptide, aptamer, or PNA probe, with a bond or force. Such a bond or force can be, for instance, a covalent bond, a hydrogen bond, an ionic bond, a metallic bond, van der Waals force, hydrophobic interaction, or planar stacking interaction. For instance, for a polypeptide probe or a nucleic acid probe attached to one or more amino acids, a reactive organoboronic moiety, such as a boronic acid, can be incorporated into lysine, asparagine, glutamine, aspartic acid, glutamic acid, serine, or cysteine residues.

Figure 2:
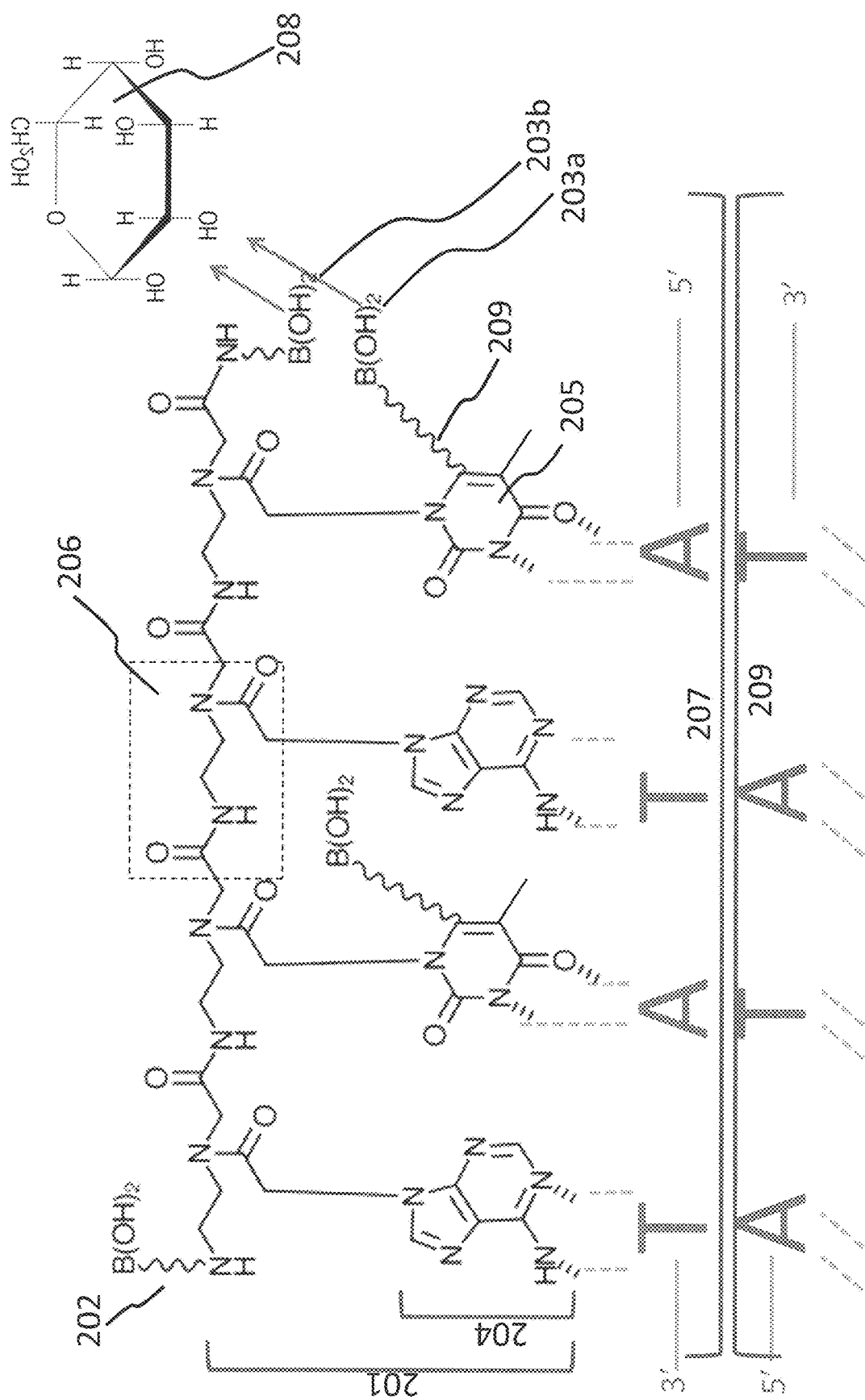
FIG. 2 provides an illustration of an embodiment wherein a double-stranded DNA is used as the polymer scaffold, and incorporated into the termini of a PNA molecule are boronic acid groups for the detection of a glucose molecule. Additionally, the nucleic acid base in the PNA capture molecule is substituted with a boronic acid reactive group, for binding to a glucose molecule. The PNA is shown base pairing with the polymer scaffold, displacing a short stretch of the complementary strand of the scaffold.
Figure 3:
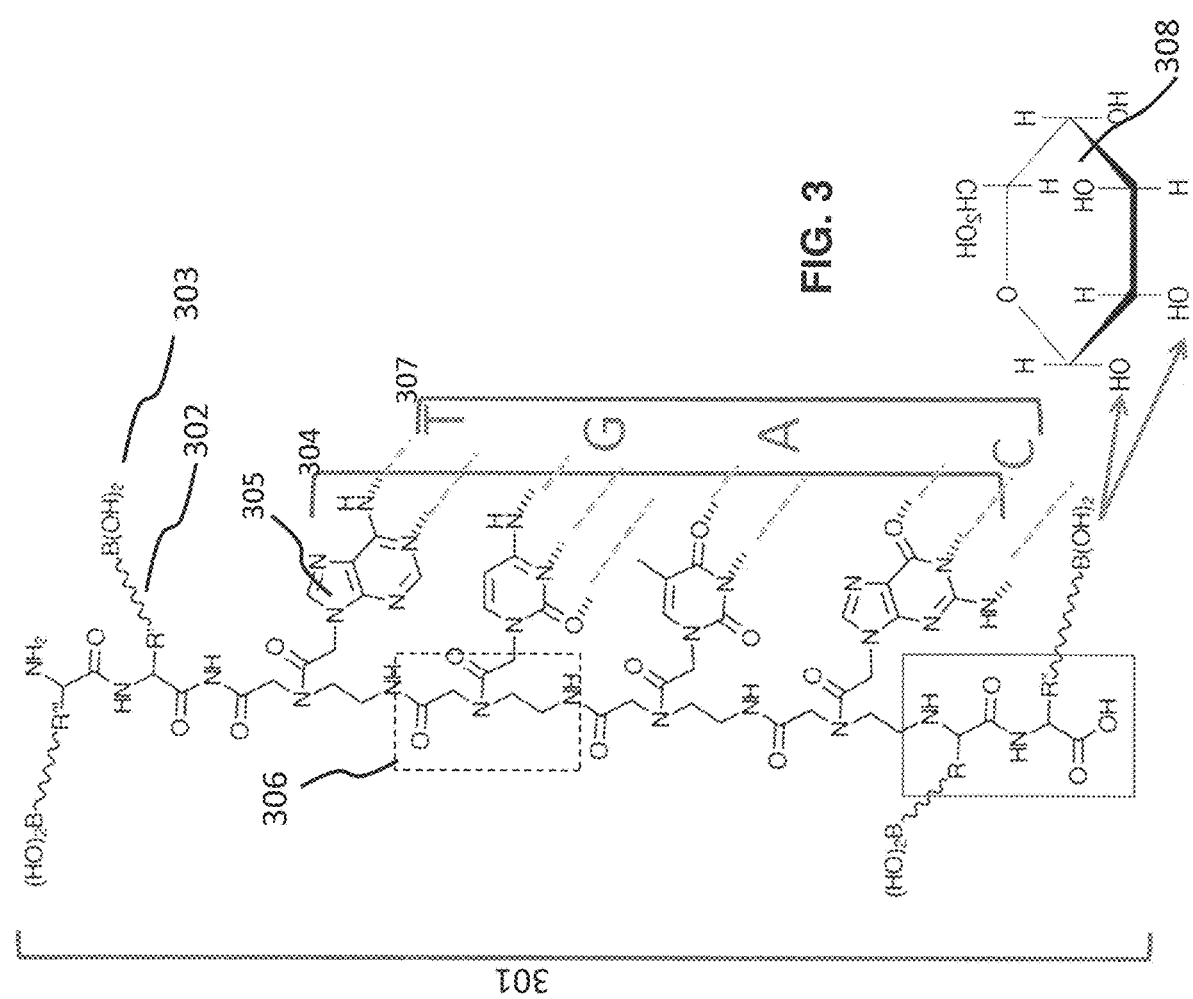
FIG. 3 provides an illustration of an embodiment wherein a double-stranded DNA is used as the polymer scaffold, and incorporated into two amino acids preceding the PNA backbone and into two amino acid residues at the end of the PNA backbone are boronic acid reactive groups for binding to a glucose molecule. The PNA is shown base pairing with the scaffold, displacing a short stretch of the complementary strand of the scaffold.

In the case the probe is a nucleic acid probe, in particular a PNA probe, FIGS. 2 and 3 illustrate how a reactive organoboronic moiety (e.g., a boronic acid) is covalently linked to the PNA. In FIGS. 2 and 3, the PNA probe 201/301 are covalently linked (202/302) to a boronic acid reactive group, 203a,b/303. This capture molecule includes a DNA binding domain 204/304, which is made up of individual bases (purines/pyrimidines), 205/305. The backbone of the PNA molecule is made up of repeating monomer units (box 206/306). The capture PNA molecule binds to a suitable nucleotide sequence on the polymer dsDNA scaffold, 207/307. The reactive boronic acid group is incorporated into the PNA molecule at 3 possible sites, the base (203a) and/or PNA backbone (203b), and/or to additional amino acids added to the PNA backbone (FIG. 3, 302). The boronic acid can be incorporated at only one position, or at all three positions, or any combination thereof. For example, FIG. 2 show boronic acid incorporated into the DNA base twice and the PNA backbone twice, for a total of 4 boronic acid substitutions. The boronic acid group can react with a sugar molecule containing a diol (208/308) that is present in a biological sample, e.g. a blood sample from a patient, for detection. The complementary strand of the DNA scaffold is displaced (209, not shown in FIG. 3). Shown in FIGS. 2 and 3 is a PNA bound to only 4 bases as an example, however, probes may bind to more than 4 bases.

Figure 4A:
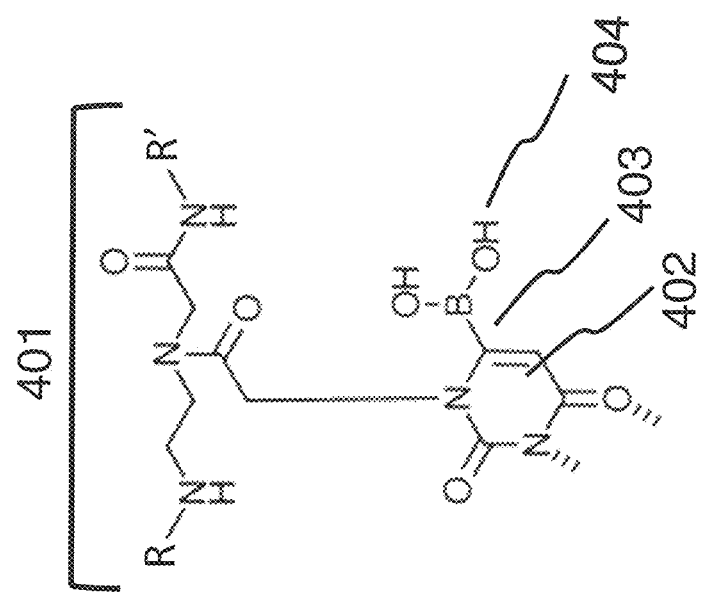
FIG. 4a provides an embodiment of a possible connectivity of the boronic acid functional group to the base uracil, and the connectivity of uracil to one unit of the PNA backbone.

FIG. 4a illustrates an embodiment of a linkage to incorporate boronic acid into the PNA molecules. In FIG. 4a boronic acid (404) is incorporated into the 5' position (403) of a pyrimidine ring (402) of uridine. This molecule is generated from a precursor that has bromine incorporated at that position, which is reacted with butyl lithium, to form a lithium substituted intermediate, and then finally turned to 5-boryluridine using tri butyl borate (W. Tjarks, J. Organomet. Chem., 2000, 614, 37., Y. Yamamoto, Pure Appl. Chem., 1991, 63, 423., Y. L. Song and C. Morin, Synlett, 2001, 266, R. F. Schinazi and W. H. Prusoff, J. Org. Chem., 1989, 50, 841., N. Goudgaon, G. Elkattan and R. Schinazi, Nucleosides, Nucleotides Nucleic Acids, 1994, 13, 849.). For context, a subunit of PNA is shown (401), along with the uridine (402).

Figure 4B:
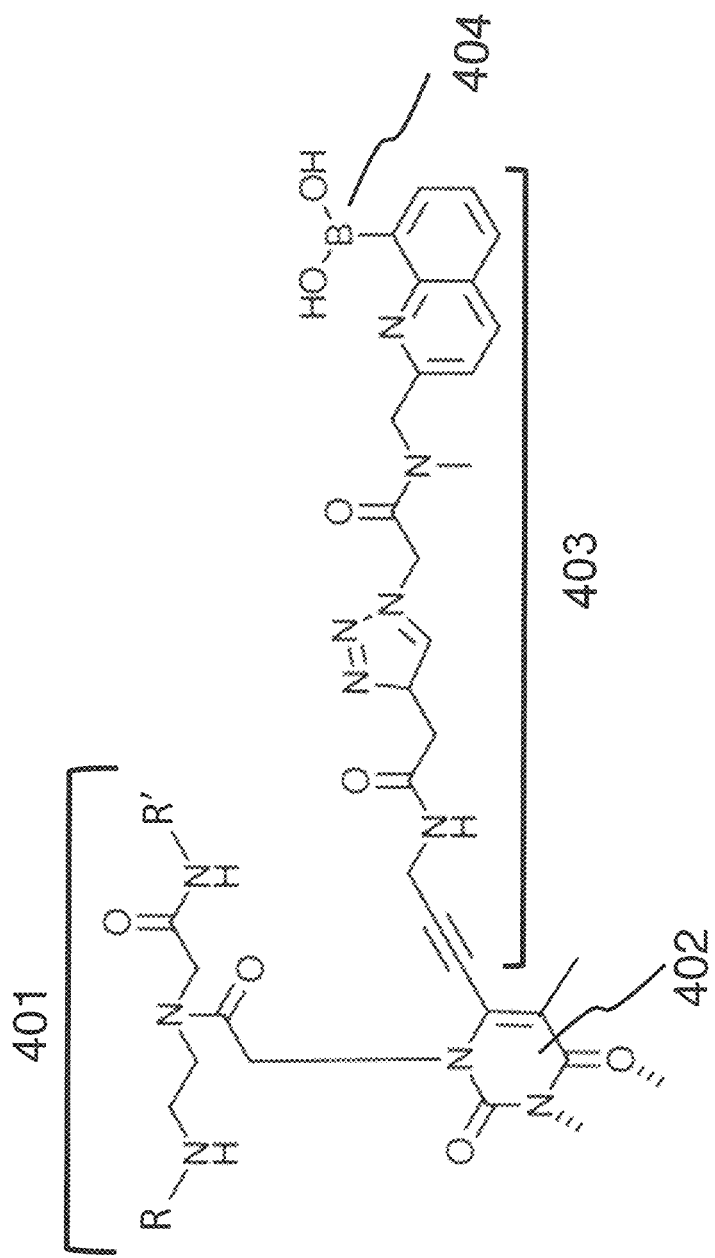
FIG. 4b provides another embodiment of a possible connectivity of the boronic acid functional group to the base thymine, and the connectivity of thymine to one unit of the PNA backbone.

FIG. 4b illustrates another embodiment of a linkage to incorporate boronic acid into the PNA molecules. In FIG. 4b boronic acid (404) is incorporated into the 5' position in the pyrimidine ring (402) using the linkage shown (403) (N. Lin, B. Wang, Nucleic Acids Research, 2007, Vol. 35, No. 4). For context a subunit of PNA is shown (401).

Figure 4C:
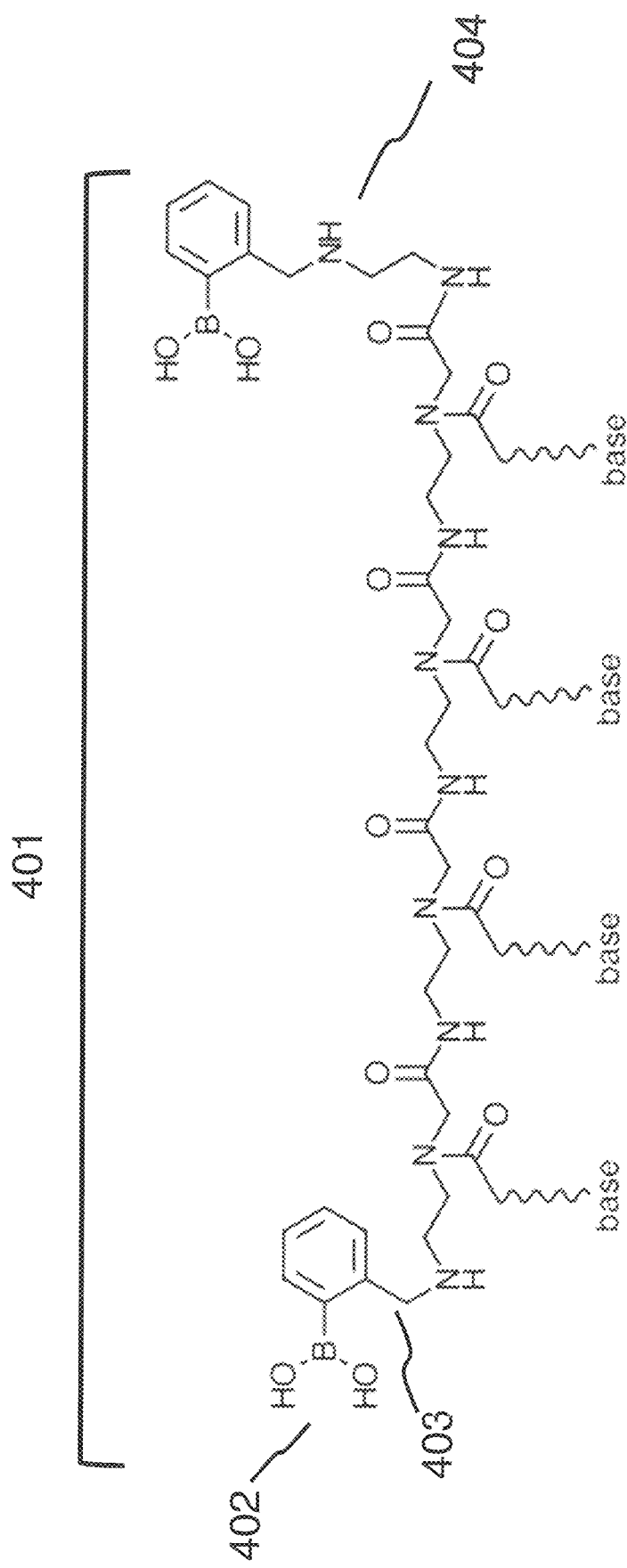
FIG. 4c provides another embodiment of a possible connectivity of the boronic acid functional group to the base amino termini of the PNA molecule FIG. 5 provides an illustration of some possible connectivities of the boronic acid functional group to the side chains of amino acids lysine, asparagine, and glutamine. A wavy line represents the PNA backbone. DNA bases are removed for clarity.

FIG. 4c illustrates another embodiment of a linkage to incorporate boronic acid into the PNA molecules. In FIG. 4c boronic acid (402) is incorporated into the amine and amide ends of the PNA backbone using linkage 403 and 404. PNA backbone is shown (401), base and linkages to bases are simplified with a wavy line and the word "base" for clarity.

Figure 5:
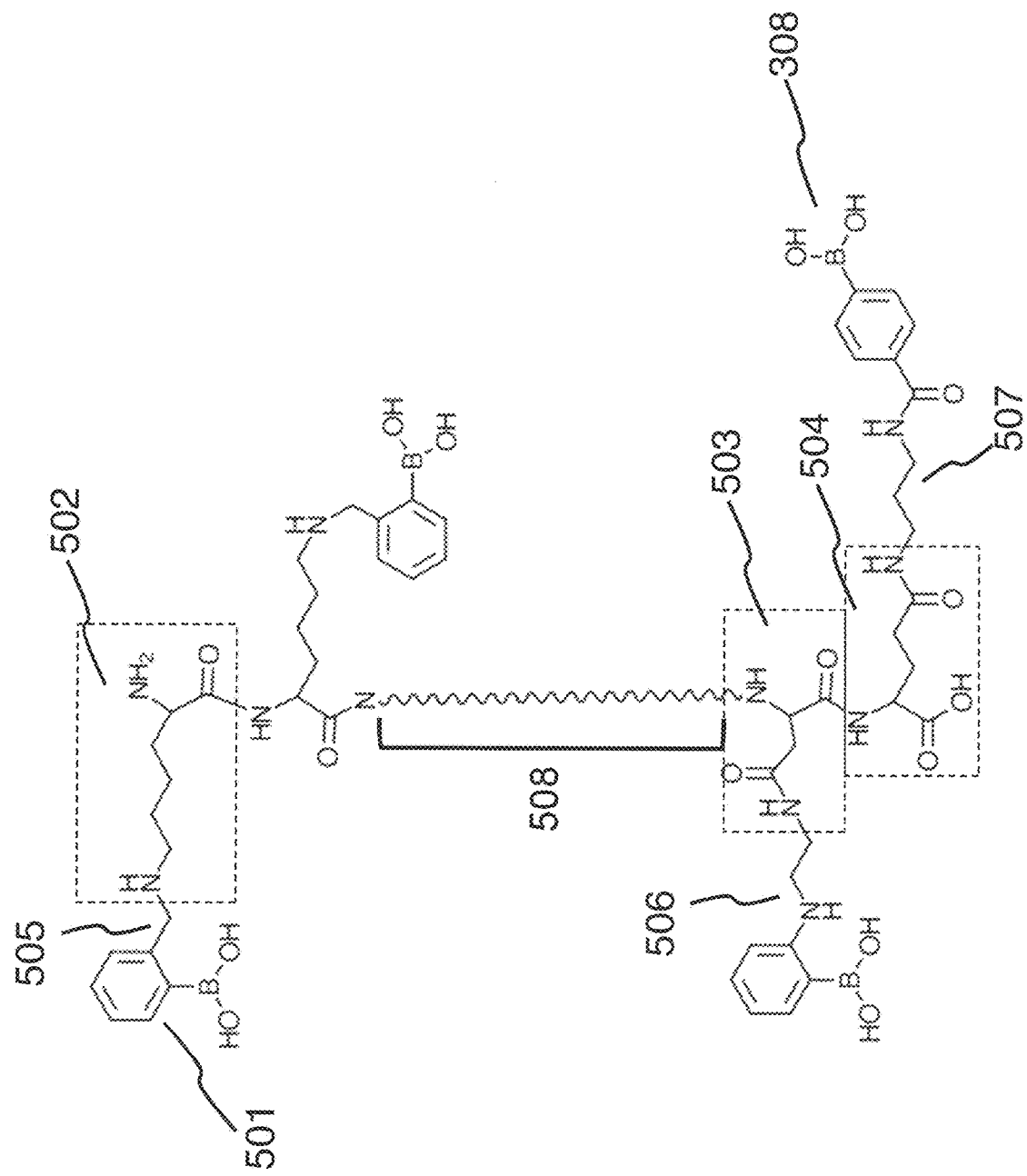

FIG. 5 illustrates three different specific linkages to incorporate boronic acid into the PNA molecule. In FIG. 5 phenyl boronic acid (501) is incorporated into the side chain of an amino acid residue. In an embodiment, phenyl boronic acid is incorporated into lysine (502) using the method as described in Edwards N Y, Sager T W, McDevitt J T, Anslyn E V. J Am Chem Soc 2007; 129:13575-13583.). In an embodiment, phenyl boronic acid is incorporated into asparagine (503) using the method as described in Sun W, Bandmann H, Schrader T. Chemistry 2007; 13: 7701-7707). In an embodiment, phenyl boronic acid is incorporated into glutamine (504) using the method described here: Roberts M C, Hanson M C, Massey A P, Karren E A, Kiser P F. Adv Mater 2007; 19:2503e7. The specific linkages are shown, 505 for linking to primary amines, and 506, and 507 for linking to amides. For context, the PNA backbone is represented as a wavy line (508). The nucleotide bases are not shown for clarity.

In some embodiments, the reactive organoboronic moiety is linked to the nucleic acid or polypeptide probe through a linker. In some aspects, the linker includes an amino acid. In some aspects, the linker is selected from a group consisting of:

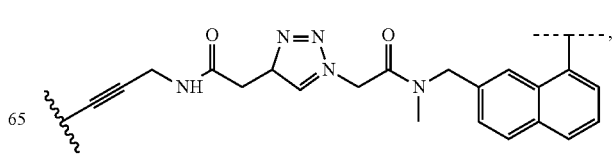

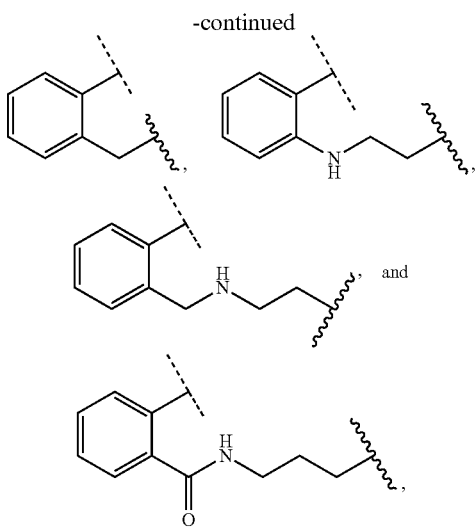

wherein ----- represents the point of connection towards the reactive organoboronic moiety and ∼∼∼ represents the point of connection towards the nucleic acid probe.

In some aspects, the linker is selected from a group consisting of:

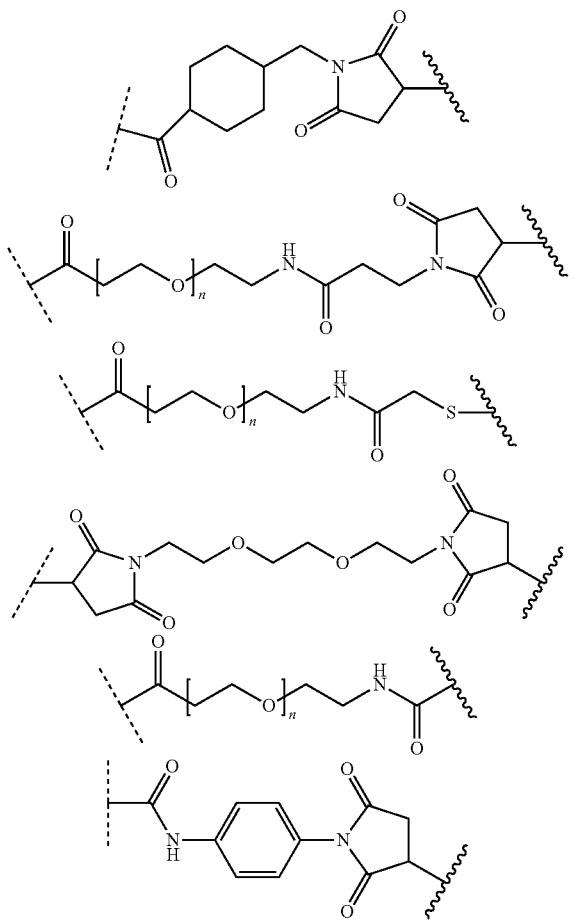

wherein ----- represents the point of connection towards the reactive organoboronic moiety and ∼∼∼ represents the point of connection towards the nucleic acid probe.

Measurement of Affinity of Binding

The present technology can also be used for measuring the binding affinity between two molecules and to determine other binding dynamics. For instance, after the binding motif passes through the pore of a nanopore device, the device can be reconfigured to reverse the movement direction of the polymer scaffold (as described below) such that the binding motif can pass through the pore again.

Prior to the binding motif entering the pore again, one can change the conditions in the sample that is loaded into the nanopore device. For instance, the condition can be one or more of changing the concentration or removing the target molecule from the sample, adding an agent that competes with the target molecule or the reactive group for binding, and changing the pH, salt, or temperature.

Under the changed conditions, the binding motif passes through the pore again. It can then be detected whether the target molecule is still bound to the capture molecule, therefore determining how the changed conditions impact the binding.

In some aspects, once the binding motif is in the pore, it is retained there while the conditions are changed, and thus the impact of the changed conditions can be measured in situ.

Alternatively or in addition, the polymer scaffold can include multiple binding motifs and each of the binding motifs can bind to a capture molecule which can bind to a target molecule. While each binding motif passes through the pore, the conditions of the sample can be changed, allowing detection of changed binding between the reactive group and the target molecule on a continued basis.

Multiplexing

In some aspects, rather than including multiple binding motif of the same kind, a polymer scaffold can include many different binding motifs that each binds a different corresponding binding domain of a capture molecule. Meanwhile, a test can include multiple types of capture molecules, each having the different binding domains. In such a configuration, many different target molecules in the same starting sample material can be detected.

In some aspects, rather than including multiple binding motif of the same kind, a polymer scaffold can include many different binding motifs that each binds a different corresponding binding domain of a capture molecule. Meanwhile, a sample can include multiple types of capture molecules, each having not only the different binding domains, but also a different reactive group (e.g. different boronic acid derivatives) capable of reacting with different target molecules. In such a configuration, many different target molecules in the same starting sample material can be detected.

Figure 7:
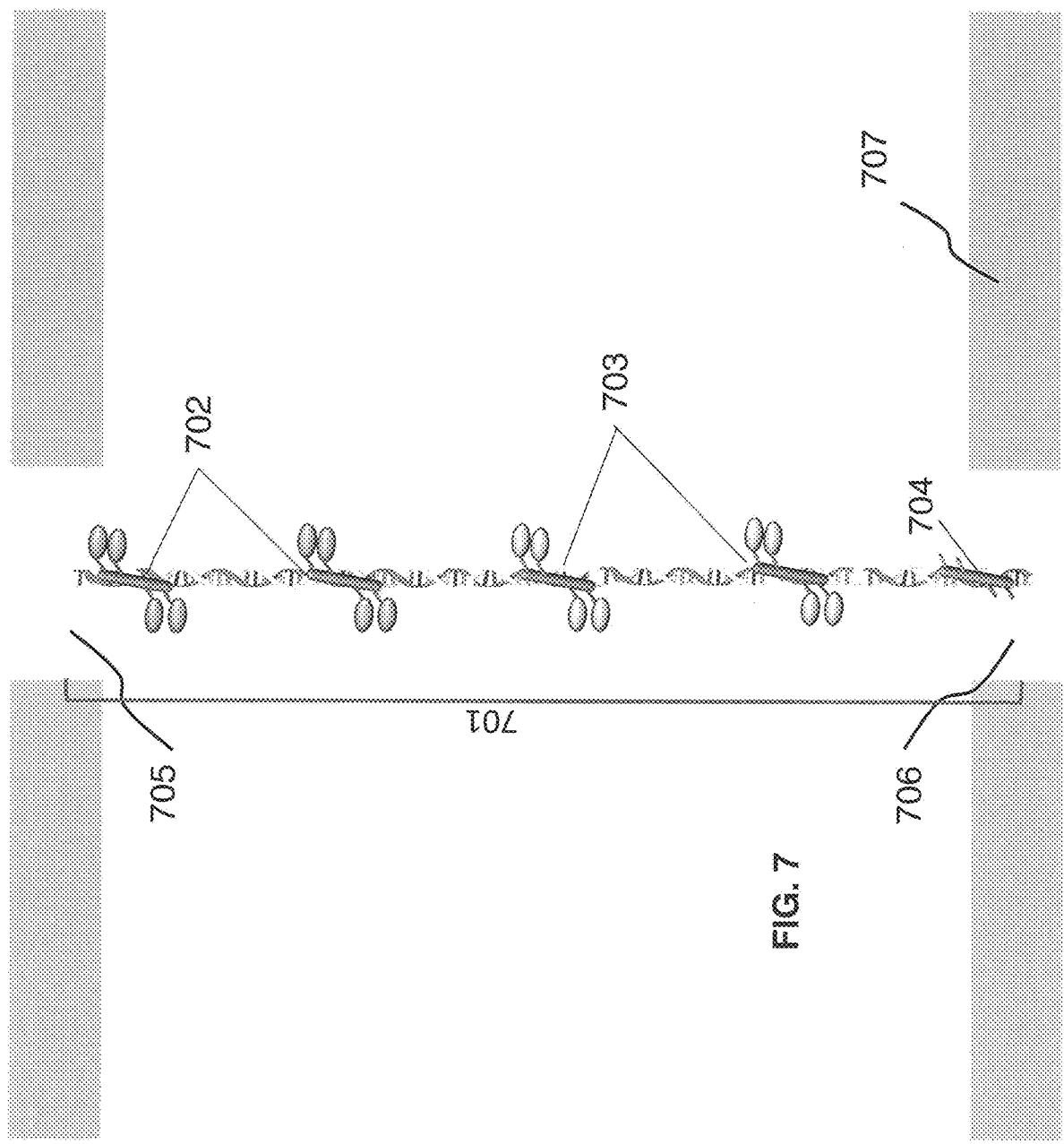
FIG. 7 illustrates an embodiment wherein the scaffold contains multiple different binding motifs that bind different capture molecules for the detection of multiple target molecules. This allows for a single scaffold to have multiplex analysis capability.

With such a setting, a single polymer scaffold can be used to detect multiple types of target molecules. FIG. 7 illustrates such a method. Here, a double-stranded DNA is used as the polymer scaffold 701, including multiple binding motifs, two copies of 702, two copies of 703, and one copy of 704.

When the DNA passes through a nanopore device that has one (705) or two coaxial pores, 705 and 706, the binding status of each of the binding motifs is detected, in which both copies of 702 show binding to a corresponding capture/target molecule complex, both copies of 703 show binding to a different corresponding capture/target molecule complex, and the capture molecule to 704 does not bind to a corresponding target molecule. Thus indicating the presence of the first two targets, while the third is absent.

This way, with a single polymer and one or more nanopore device, the present technology can detect different target molecules. Further, by determining how many copies of binding motifs are bound by a capture/target molecule complex, and by tuning conditions that impact the bindings, the system can obtain more detailed binding dynamic information, such as binding affinity (Kd) or concentration of the target molecule.

Nanopore Devices

A nanopore device, as provided, includes at least one pore that forms an opening in a structure separating an interior space of the device into two volumes, and at least one sensor configured to identify objects (for example, by detecting changes in parameters indicative of objects) passing through the pore.

The pore(s) in the nanopore device are of a nano scale or micro scale. In one aspect, each pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In some aspects, each pore is at least about 100 nm, 200 nm, 500 nm, 1000 nm, 2000 nm, 3000 nm, 5000 nm, 10000 nm, 20000 nm, or 30000 nm in diameter. In one aspect, the pore is no more than about 100000 nm in diameter. Alternatively, the pore is no more than about 50000 nm, 40000 nm, 30000 nm, 20000 nm, 10000 nm, 9000 nm, 8000 nm, 7000 nm, 6000 nm, 5000 nm, 4000 nm, 3000 nm, 2000 nm, or 1000 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore(s) in the nanopore device are of a larger scale for detecting large microorganisms or cells. In one aspect, each pore has a size that allows a large cell or microorganism to pass. In one aspect, each pore is at least about 100 nm in diameter. Alternatively, each pore is at least about 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, or 5000 nm in diameter.

In one aspect, the pore is no more than about 100,000 nm in diameter. Alternatively, the pore is no more than about 90,000 nm, 80,000 nm, 70,000 nm, 60,000 nm, 50,000 nm, 40,000 nm, 30,000 nm, 20,000 nm, 10,000 nm, 9000 nm, 8000 nm, 7000 nm, 6000 nm, 5000 nm, 4000 nm, 3000 nm, 2000 nm, or 1000 nm in diameter.

In one aspect, the pore has a diameter that is between about 100 nm and about 10000 nm, or alternatively between about 200 nm and about 9000 nm, or between about 300 nm and about 8000 nm, or between about 400 nm and about 7000 nm, or between about 500 nm and about 6000 nm, or between about 1000 nm and about 5000 nm, or between about 1500 nm and about 3000 nm.

In some aspects, the nanopore device further includes electronics and logic to move a polymer scaffold across the pore and/or means to identify objects that pass through the pore. Further details are provided below, described in the context of a two-pore device.

Compared to a single-pore nanopore device, a two-pore device can be more easily configured to provide control of speed and direction of the movement of the polymer across the pores.

In an embodiment, the nanopore device includes a plurality of chambers, each chamber in communication with an adjacent chamber through at least one pore. Among these pores, two pores, namely a first pore and a second pore, are placed so as to allow at least a portion of a polymer to move out of the first pore and into the second pore. Further, the device includes a sensor capable of identifying the polymer during the movement. In one aspect, the identification entails identifying individual components of the polymer. In another aspect, the identification entails identifying fusion molecules and/or target molecules bound to the polymer. When a single sensor is employed, the single sensor may include two electrodes placed at both ends of a pore to measure an ionic current across the pore. In another embodiment, the single sensor comprises a component other than electrodes.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymers to move from one chamber to the next simultaneously. Such a multi-pore design can enhance throughput of polymer analysis in the device.

In some aspects, the device further includes means to move a polymer from one chamber to another. In one aspect, the movement results in loading the polymer across both the first pore and the second pore at the same time. In another aspect, the means further enables the movement of the polymer, through both pores, in the same direction.

For instance, in a three-chamber two-pore device (a "two-pore" device), each of the chambers can contain an electrode for connecting to a power supply so that a separate voltage can be applied across each of the pores between the chambers.

In accordance with an embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore. Such a device may have any of the dimensions or other characteristics previously disclosed in U.S. Publ. No. 2013/0233709, entitled Dual-Pore Device, which is herein incorporated by reference in its entirety.

Figure 8A:
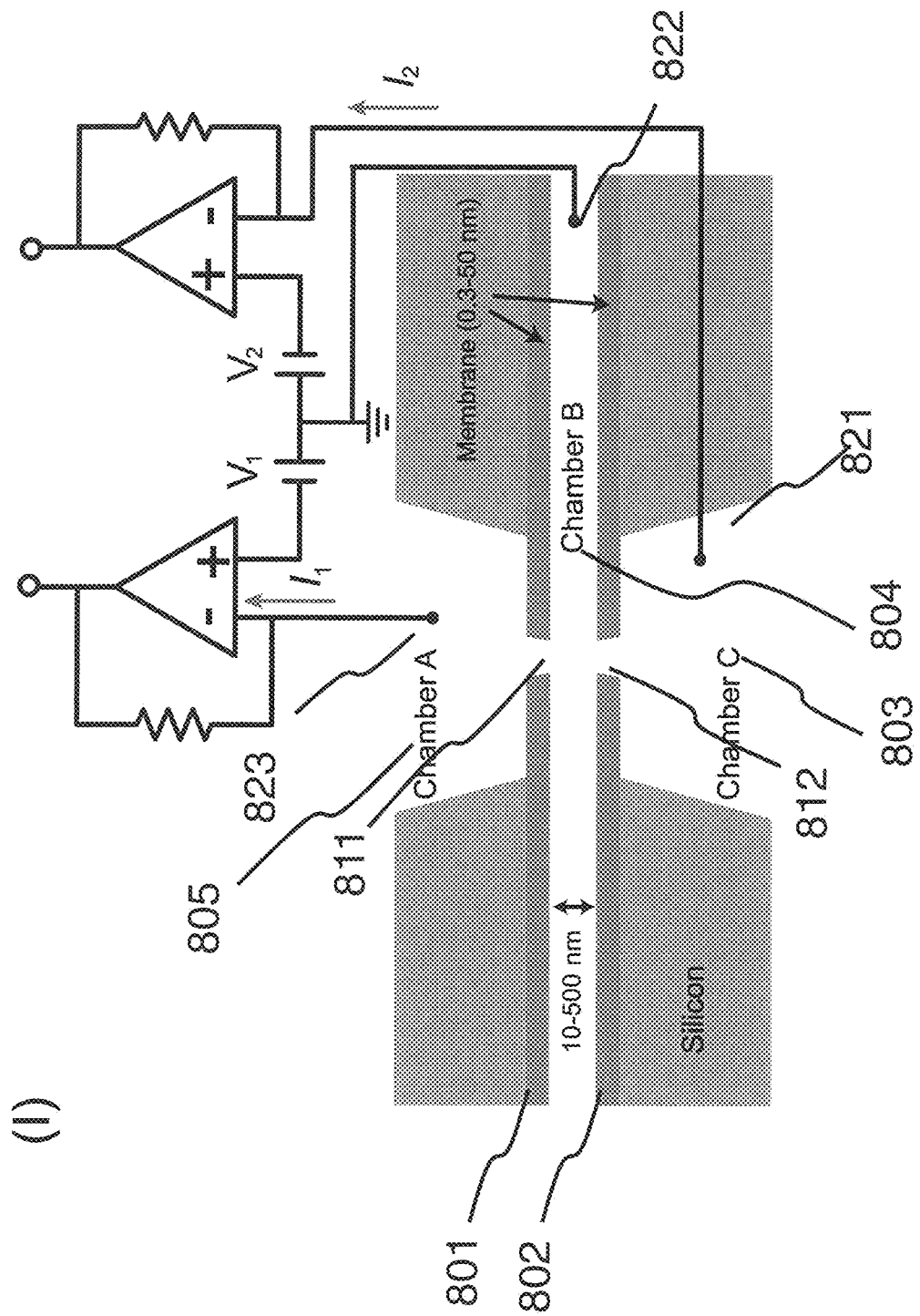
FIGS. 8a-c illustrate a nanopore device with at least two pores separating multiple chambers.

In some embodiments as shown in FIG. 8a, the device includes an upper chamber 805 (Chamber A), a middle chamber 804 (Chamber B), and a lower chamber 803 (Chamber C). The chambers are separated by two separating layers or membranes (801 and 802) each having a separate pore (811 or 812). Further, each chamber contains an electrode (821, 822 or 823) for connecting to a power supply. The annotation of upper, middle and lower chamber is in relative terms and does not indicate that, for instance, the upper chamber is placed above the middle or lower chamber relative to the ground, or vice versa.

Each of the pores 811 and 812 independently has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In other aspects, each pore is at least about 100 nm, 200 nm, 500 nm, 1000 nm, 2000 nm, 3000 nm, 5000 nm, 10000 nm, 20000 nm, or 30000 nm in diameter. In one aspect, each pore is 50,000 nm to 100,000 nm in diameter. In one aspect, the pore is no more than about 100000 nm in diameter. Alternatively, the pore is no more than about 50000 nm, 40000 nm, 30000 nm, 20000 nm, 10000 nm, 9000 nm, 8000 nm, 7000 nm, 6000 nm, 5000 nm, 4000 nm, 3000 nm, 2000 nm, or 1000 nm in diameter.

In some aspects, the pore has a substantially round shape. "Substantially round," as used here, refers to a shape that is at least about 80 or 90% in the form of a cylinder. In some embodiments, the pore is square, rectangular, triangular, oval, or hexagular in shape.

Each of the pores 811 and 812 independently has a depth (i.e., a length of the pore extending between two adjacent volumes). In one aspect, each pore has a depth that is least about 0.3 nm. Alternatively, each pore has a depth that is at least about 0.6 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm.

In one aspect, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm.

In one aspect, the pore has a depth that is between about 1 nm and about 100 nm, or alternatively, between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the nanopore extends through a membrane. For example, the pore may be a protein channel inserted in a lipid bilayer membrane or it may be engineered by drilling, etching, or otherwise forming the pore through a solid-state substrate such as silicon dioxide, silicon nitride, grapheme, or layers formed of combinations of these or other materials. In some aspects, the length or depth of the nanopore is sufficiently large so as to form a channel connecting two otherwise separate volumes. In some such aspects, the depth of each pore is greater than 100 nm, 200 nm, 300 nm, 400 nm, 500 nm, 600 nm, 700 nm, 800 nm, or 900 nm. In some aspects, the depth of each pore is no more than 2000 nm or 1000 nm.

In one aspect, the pores are spaced apart at a distance that is between about 10 nm and about 1000 nm. In some aspects, the distance between the pores is greater than 1000 nm, 2000 nm, 3000 nm, 4000 nm, 5000 nm, 6000 nm, 7000 nm, 8000 nm, or 9000 nm. In some aspects, the pores are spaced no more than 30000 nm, 20000 nm, or 10000 nm apart. In one aspect, the distance is at least about 10 nm, or alternatively, at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm.

In yet another aspect, the distance between the pores is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no direct blockage between them. Still, in one aspect, the pores are substantially coaxial, as illustrated in FIG. 8a.

In one aspect, as shown in FIG. 8a, the device, through the electrodes 821, 822, and 823 in the chambers 803, 804, and 805, respectively, is connected to one or more power supplies. In some aspects, the power supply includes a voltage-clamp or a patch-clamp, which can supply a voltage across each pore and measure the current through each pore independently. In this respect, the power supply and the electrode configuration can set the middle chamber to a common ground for both power supplies. In one aspect, the power supply or supplies are configured to apply a first voltage V1 between the upper chamber 805 (Chamber A) and the middle chamber 804 (Chamber B), and a second voltage V2 between the middle chamber 804 and the lower chamber 803 (Chamber C).

In some aspects, the first voltage V1 and the second voltage V2 are independently adjustable. In one aspect, the middle chamber is adjusted to be a ground relative to the two voltages. In one aspect, the middle chamber comprises a medium for providing conductance between each of the pores and the electrode in the middle chamber. In one aspect, the middle chamber includes a medium for providing a resistance between each of the pores and the electrode in the middle chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the upper chamber to the middle chamber and to the lower chamber, or the other way around, sequentially. In some aspects, when the two voltages are set to opposite polarity, a charged particle can be moved from either the upper or the lower chamber to the middle chamber and kept there.

The adjustment of the voltages in the device can be particularly useful for controlling the movement of a large molecule, such as a charged polymer, that is long enough to cross both pores at the same time. In such an aspect, the direction and the speed of the movement of the molecule can be controlled by the relative magnitude and polarity of the voltages as described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, TiO2, HfO2, Al2O3, or other metallic layers, or any combination of these materials. In some aspects, for example, a single sheet of graphene membrane of about 0.3 nm thick can be used as the pore-bearing membrane.

Figure 8C:
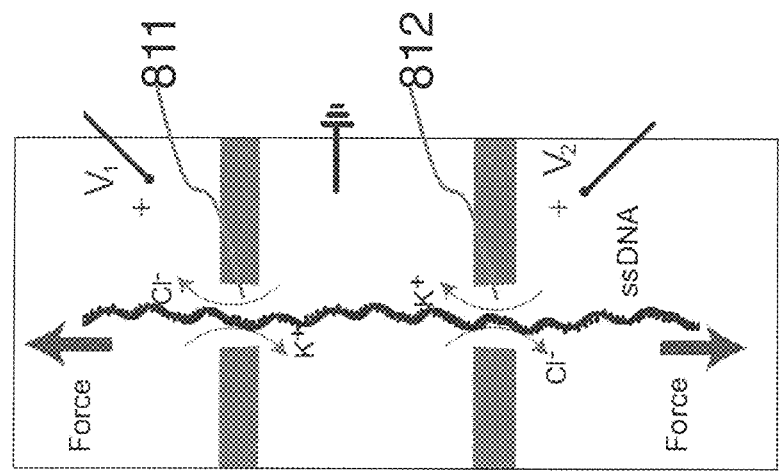
Figure 8B:
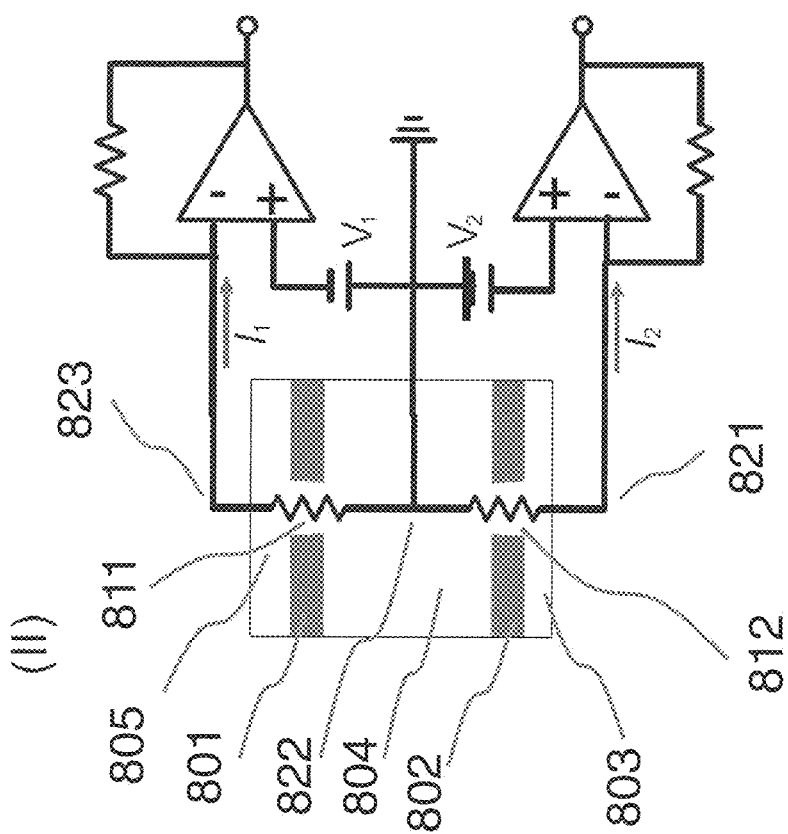

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C. In one aspect, as shown in FIG. 8b, the housing would provide minimal access resistance between the voltage electrodes 821, 822, and 823 and the nanopores 811 and 812, to ensure that each voltage is applied principally across each pore.

In one aspect, the device includes a microfluidic chip (labeled as "Dual-pore chip") comprising two parallel membranes connected by spacers. Each membrane contains a pore drilled by a single beam through the center of the membrane. Further, the device preferably has a Teflon® housing for the chip. The housing ensures sealed separation of Chambers A-C and provides minimal access resistance for the electrode to ensure that each voltage is applied principally across each pore.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath comprising the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

In another aspect, the insertion of biological nanopores into solid-state nanopores to form a hybrid pore can be used in either or both pores in the two-pore method. The biological pore can increase the sensitivity of the ionic current measurements, and is useful when only single-stranded polynucleotides are to be captured and controlled in the two-pore device, e.g., for sequencing.

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber.

One example concerns a charged polymer scaffold, such as a DNA, having a length that is longer than the combined distance that includes the depth of both pores plus the distance between the two pores. For example, a 1000 bp dsDNA is about 340 nm in length, and would be substantially longer than the 40 nm spanned by two 10 nm-deep pores separated by 20 nm. In a first step, the polynucleotide is loaded into either the upper or the lower chamber. By virtue of its negative charge under a physiological condition at a pH of about 7.4, the polynucleotide can be moved across a pore on which a voltage is applied. Therefore, in a second step, two voltages, in the same polarity and at the same or similar magnitudes, are applied to the pores to move the polynucleotide across both pores sequentially.

At about the time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of polarity of the voltage at the first pore, therefore, will generate a force that pulls the polynucleotide away from the second pore as illustrated in FIG. 8c.

Assuming that the two pores have identical voltage-force influence and $|V1|=|V2|+\delta V$, the value $\delta V>0$ (or <0) can be adjusted for tunable motion in the V1 (or V2) direction. In practice, although the voltage-induced force at each pore will not be identical with V1=V2, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications.

Accordingly, in one aspect, provided is a method for controlling the movement of a charged polymer through a nanopore device. The method entails (a) loading a sample comprising a charged polymer in one of the upper chamber, middle chamber or lower chamber of the device of any of the above embodiments, wherein the device is connected to one or more power supplies for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber (voltage-competition mode), wherein the two voltages are different in magnitude, under controlled conditions, so that the charged polymer moves across both pores in either direction and in a controlled manner.

To establish the voltage-competition mode in step (c), the relative force exerted by each voltage at each pore is to be determined for each two-pore device used, and this can be done with calibration experiments by observing the influence of different voltage values on the motion of the polynucleotide, which can be measured by sensing known-location and detectable features in the polynucleotide, with examples of such features detailed in this application. If the forces are equivalent at each common voltage, for example, then using the same voltage value at each pore (with common polarity in upper and lower chambers relative to grounded middle chamber) creates a zero net motion in the absence of thermal agitation. If the forces are not equivalent at each common voltage, achieving equal forces involves the identification and use of a larger voltage at the pore that experiences a weaker force at the common voltage. Calibration for voltage-competition mode can be done for each two-pore device, and for specific charged polymers or molecules whose features influence the force when passing through each pore.

In one aspect, the sample containing the charged polymer is loaded into the upper chamber and the initial first voltage is set to pull the charged polymer from the upper chamber to the middle chamber and the initial second voltage is set to pull the polymer from the middle chamber to the lower chamber. Likewise, the sample can be initially loaded into the lower chamber, and the charged polymer can be pulled to the middle and the upper chambers.

In another aspect, the sample containing the charged polymer is loaded into the middle chamber; the initial first voltage is set to pull the charged polymer from the middle chamber to the upper chamber; and the initial second voltage is set to pull the charged polymer from the middle chamber to the lower chamber.

In one aspect, the adjusted first voltage and second voltage at step (c) are about 10 times to about 10,000 times as high, in magnitude, as the difference/differential between the two voltages. For instance, the two voltages can be 90 mV and 100 mV, respectively. The magnitude of the two voltages, about 100 mV, is about 10 times of the difference/differential between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference/differential between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference/differential between them.

In one aspect, real-time or on-line adjustments to the first voltage and the second voltage at step (c) are performed by active control or feedback control using dedicated hardware and software, at clock rates up to hundreds of megahertz. Automated control of the first or second or both voltages is based on feedback of the first or second or both ionic current measurements.

Sensors

As discussed above, in various aspects, the nanopore device further includes one or more sensors to carry out the identification of the binding status of the binding motifs.

The sensors used in the device can be any sensor suitable for identifying a molecule or particle, such as a polymer. For instance, a sensor can be configured to identify the polymer by measuring a current, a voltage, a pH value, an optical feature, or residence time associated with the polymer. In other aspects, the sensor may be configured to identify one or more individual components of the polymer or one or more components bound to the polymer. The sensor may be formed of any component configured to detect a change in a measurable parameter where the change is indicative of the polymer, a component of the polymer, or preferably, a component bound to the polymer. In one aspect, the sensor includes a pair of electrodes placed at two sides of a pore to measure an ionic current across the pore when a molecule or particle, in particular a polymer, moves through the pore. In certain aspects, the ionic current across the pore changes measurably when a polymer segment passing through the pore is bound to a fusion molecule and/or fusion molecule-target molecule complex. Such changes in current may vary in predictable, measurable ways corresponding with, for example, the presence, absence, and/or size of the fusion molecules and target molecules present.

In an embodiment, the sensor measures an optical feature of the polymer, a component (or unit) of the polymer, or a component bound to the polymer. One example of such measurement includes the identification of an absorption band unique to a particular unit by infrared (or ultraviolet) spectroscopy.

When residence time measurements are used, the size of the component can be correlated to the specific component based on the length of time it takes to pass through the sensing device.

Still further, in embodiments directed towards detecting units of the polymer, the sensor can include an enzyme distal to the sensing device, where the enzyme is capable of separating the terminal unit of the polymer from the penultimate unit, thereby providing for a single molecular unit of the polymer. The single molecule, such as a single nucleotide or an amino acid, can then translocate through the pore and may or may not be detected. However, when the enzyme encounters a bound target molecule, the enzyme will not be able to cleave the penultimate unit, and therefore will become stalled or will skip to the next available cleavage sites, thus releasing a fragment that has a comparable size difference from a single unit and is thus detectable. Detection can be done with sensors as described in this application or detected with methods such as mass spectrometry. Methods for measuring such units are known in the art and include those developed by Cal Tech (see, e.g., spectrum.ieee.org/tech-talk/at-work/test-and-measurement/a-scale-for-weighing-single-molecules). The results of such analysis can be compared to those of the sensing device to confirm the correctness of the analysis.

In some embodiments, the sensor is functionalized with reagents that form distinct non-covalent bonds with each association site or each associated target molecule. In this respect, the gap is large enough to allow effective measuring. For instance, when a sensor is functionalized with reagents to detect a feature on DNA that is 5 nm on a dsDNA scaffold, a 7.5 nm gap can be used, because DNA is 2.5 nm wide.

Tunnel sensing with a functionalized sensor is termed "recognition tunneling." Using current technology, a Scanning Tunneling Microscope (STM) with recognition tunneling identifies a DNA base flanked by other bases in a short DNA oligomer. As has been described, recognition tunneling can provide a "universal reader" designed to hydrogen-bond in a unique orientation to molecules that a user desires to be detected. Most reported is the identification of nucleic acids; however, it is herein modified to be employed to detect target molecules on a scaffold.

A limitation with the conventional recognition tunneling is that it can detect only freely-diffusing molecules that randomly bind in the gap, or that happen to be in the gap during microscope motion, with no method of explicit capture in the gap. However, the collective drawbacks of the STM setup can be eliminated by incorporating the recognition reagent, optimized for sensitivity, within an electrode tunneling gap in a nanopore channel.

Accordingly, in an embodiment, the sensor includes surface modification by a reagent. In one aspect, the reagent is capable of forming a non-covalent bond with an association site or an attached target molecule. In a particular aspect, the bond is a hydrogen bond. Non-limiting examples of the reagent include 4-mercaptobenzamide and 1-H-Imidazole-2-carboxamide.

Furthermore, the methods of the present technology can provide DNA delivery rate control for one or more recognition tunneling sites, each positioned in one or both of the nanopore channels, and voltage control can ensure that each target molecule resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can sequence the translocating DNA.

In some embodiments, the tunnel gap has a width from about 1 nm to about 20 nm. In one aspect, the width of the gap is at least about 1 nm, or alternatively, at least about 1.5, 2, 2.5, 3, 3.5, 4, 4.5, 5, 6, 7, 8, 9, 10, 12, or 15 nm. In another aspect, the width of the gap is not greater than about 20 nm, or alternatively, not greater than about 19, 18, 17, 16, 15, 14, 13, 12, 11, 10, 9, 8, 7, 6, 5, 4, 3, or 2 nm. In some aspects, the width is between about 1 nm and about 15 nm, between about 1 nm and about 10 nm, between about 2 nm and about 10 nm, between about 2.5 nm and about 10 nm, or between about 2.5 nm and about 5 nm.

In other embodiments, the tunnel gap is suitable for detecting micro-sized particles (e.g., viruses, bacteria, and/or cells) and has a width from about 1000 nm to about 100,000 nm. In some embodiments, the width of the gap is between about 10,000 nm and 80,000 nm or between about 20,000 nm and 50,000 nm. In another embodiment, the width of the gap is between about 50,000 nm and 100,000 nm. In some embodiments, the width of the gap is not greater than about 100,000 nm, 90,000 nm, 80,000 nm, 70,000 nm, 60,000 nm, 50,000 nm, 40,000 nm, 30,000 nm, 20,000 nm, 10,000 nm, 9000 nm, 8000 nm, 7000 nm, 6000 nm, 5000 nm, 4000 nm, 3000 nm, 2000 nm, or 1000 nm.

In some embodiments, the sensor is an electric sensor. In some embodiments, the sensor detects a fluorescent detection means when the target molecule or the detectable label passing through has a unique fluorescent signature. A radiation source at the outlet of the pore can be used to detect that signature.

EXAMPLES

The present technology is further exemplified by reference to the following example and experiments, which are not to be interpreted as limiting the scope of the invention. It will be apparent to those skilled in the art that many modifications may be practiced without departing from the scope of the current invention Example 1—DNA Alone in Solid-State Nanopore Experiment Nanopore instruments use a sensitive voltage-clamp amplifier to apply a voltage V across the pore while measuring the ionic current $I_O$ through the open pore (FIG. 9a). When a single charged molecule such as a double-stranded DNA (dsDNA) is captured and driven through the pore by electrophoresis (FIG. 9b), the measured current shifts from $I_O$ to $I_B$, and the shift amount $\Delta I=I_O-I_B$ and duration $t_D$ are used to characterize the event. After recording many events during an experiment, distributions of the events (FIG. 9c) on a $\Delta I$ vs. $t_D$ plot are analyzed to characterize the corresponding molecule in a population on the plot. In this way, nanopores provide a simple, label-free, purely electrical single-molecule method for biomolecular sensing.

We constructed a solid state nanopore as shown in FIG. 9a, showing a single 40 nm diameter nanopore fabricated in 100 nm thick silicon nitride (SiN) SiN membrane. In FIG. 9b, the representative current trace shows a blockade event caused by a 5.6 kb dsDNA passed in a single file manner (unfolded) through an 11 nm diameter nanopore in 10 nm thick SiN at 200 mV in buffer containing 1 M KCl. The mean open channel current was $I_O$=9.6 nA, with mean event amplitude $I_B$=9.1 nA, and mean event duration $t_D$=0.064 ms. The amplitude shift from the translocation of a dsDNA molecule through the nanopore was $\Delta I=I_O-I_B$=0.5 nA. In FIG. 9c, the scatter plot shows $|\Delta I|$ vs. tD for all 1301 events recorded over 16 minutes.

Figure 10A:
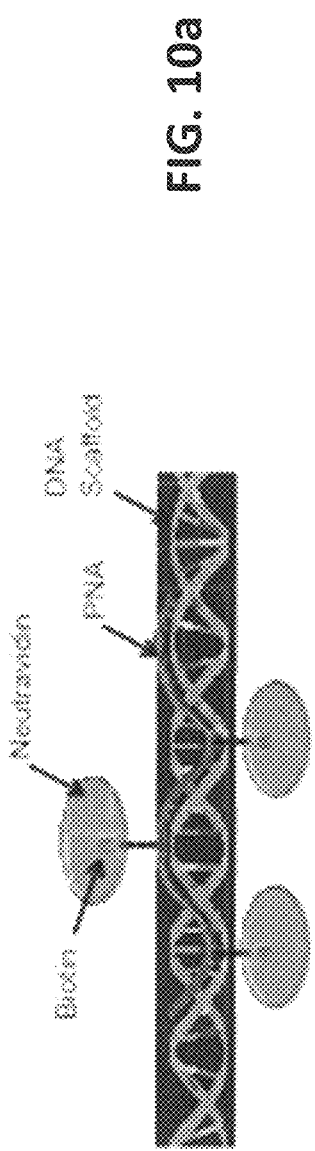
FIG. 10a is an illustration of a scaffold that binds to a capture complex of PNA bound to biotin, where the biotin specifically binds to neutravidin.
Figure 10B:
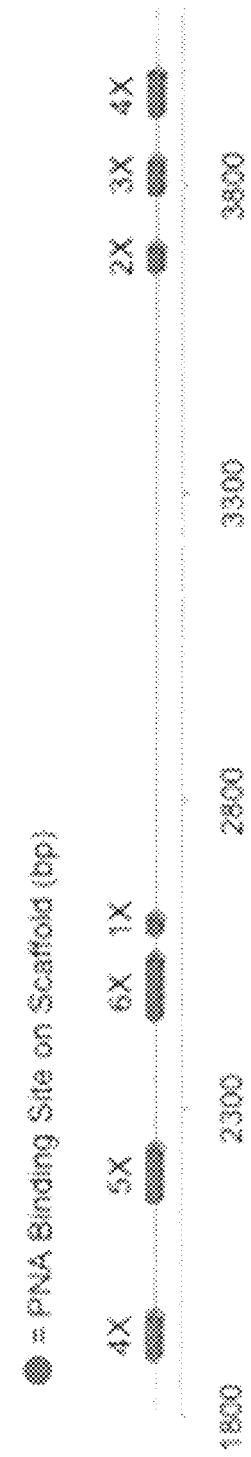
FIG. 10(b) represents the PNA binding site located on the scaffold.
Figure 11C:
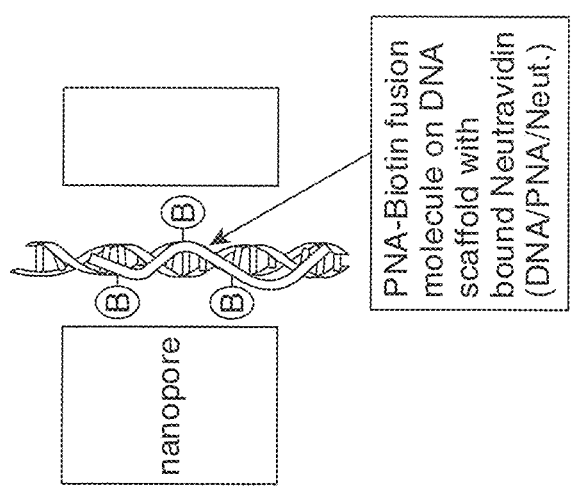
FIG. 11 shows biomolecules that pass through the nanopore (a-c) and their associated current signature (d).
Figure 11B:
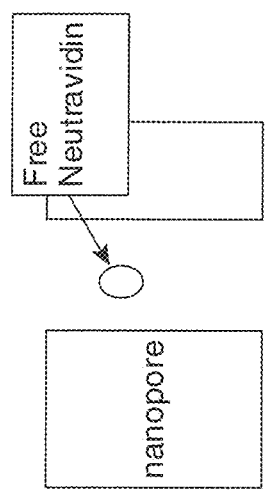
Figure 11A:
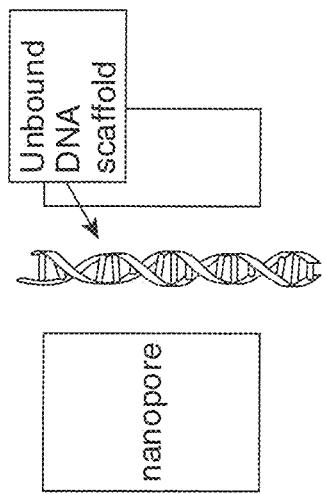
Figure 11D:
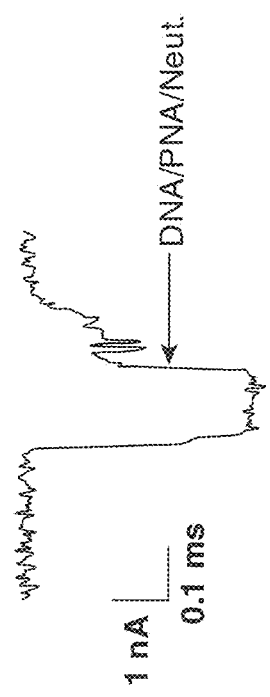

Example 2—Capture Molecules Comprising PNA and Biotin for Target Protein Detection In this example, we demonstrate use of a PNA probe that has been modified to contain a biotin moiety linked to a lysine residue in the probe to detect neutravidin in solution using the nanopore. To capture neutravidin and detect in the nanopore, we used a 5.6 kb dsDNA scaffold that is engineered to bind 12-mer peptide-nucleic-acid (PNA) molecules. Each PNA had 3 biotinylated sites for binding an avidin family member (e.g., neutravidin, and or monovalent streptavidin) (FIG. 10a). The 5.6 kb dsDNA scaffold had 25 distinct sites (binding motifs) that bound to the PNA probe to form up to 75 avidin biomarker binding sites on each scaffold (FIG. 10b).

In this setup, the capture molecule contains two separate binding domains, one that bound to a unique DNA sequence and another that bound to Neutravidin protein. The DNA binding domain was a protein nucleic acid molecule (PNA) that binds to the unique sequence (GAAAGTGAAAGT (SEQ ID NO: 1), uSeq1) that was repeated 25 times throughout the scaffold (e). The PNA used in the experiment had the sequence GAA*AGT*GAA*AGT (SEQ ID NO: 1) where the * indicates that a biotin was incorporated into the PNA backbone at the gamma position by coupling to a lysine amino acid, and thus, each PNA had three biotin molecules (PNABio). To create the fusion molecule-bound scaffold, a 60 nM scaffold was heated to 95° C. for 2 minutes, cooled to 60° C. and incubated with a 10x excess of PNA to possible PNA-binding sites on the scaffold in 15 mM NaCl for 1 hr and then cooled to 4° C. The excess PNA was dialyzed out (20 k MWCO, Thermo Scientific) for 2 hrs against 10 mM Tris pH 8.0. This DNA/PNA complex was then labeled with a 10-fold excess Neutravidin protein (Pierce/Thermo Scientific) to possible biotin sites bound to the scaffolds (assuming a 60% reduction of PNA during dialysis). The reaction was electrophoresed as described above to assess purity, concentration, and potential aggregation. This reagent, DNA/PNA/Neutravidin (D/P/N), was stored at −20° C. until use.

Representative data (FIG. 11) collected from our experiments shows that the DNA/PNA/Neutravidin complexes caused event signatures that are detectable above other background event types (e.g., unbound DNA alone, Neutravidin alone, PNA/Neutravidin alone) and can therefore be tagged as fully assembled (i.e. DNA/PNA/Neutravidin complex) events. Thus, we showed that DNA/PNA/Neutravidin complexes can be detected with a nanopore with high confidence, thereby detecting neutravidin in solution.

Figure 12A:
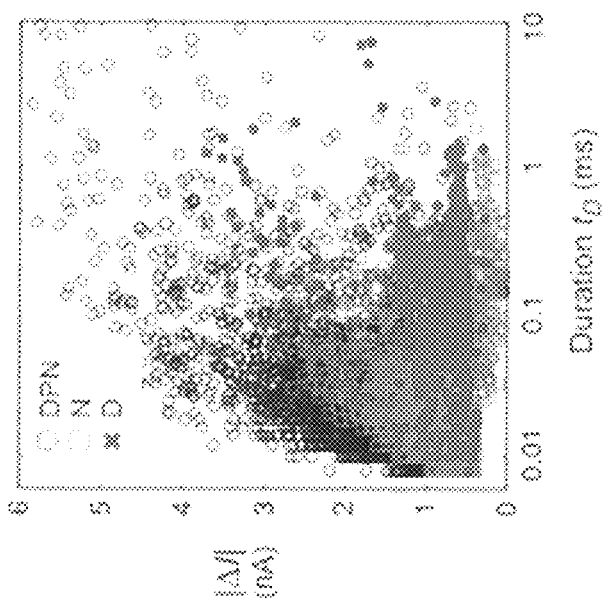
FIG. 12a shows data comparing $\Delta I$ vs. $t_D$ distributions from three separate experiments: DNA alone, Neutravidin alone, and DNA/PNA/Neutravidin complex reagents.
Figure 12B:
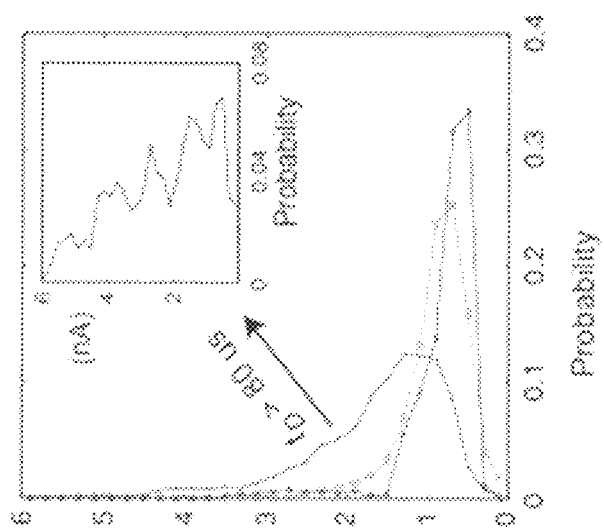
FIG. 12b shows the probability distribution of dwell time for each population of molecules captured in the nanopore.
Figure 12C:
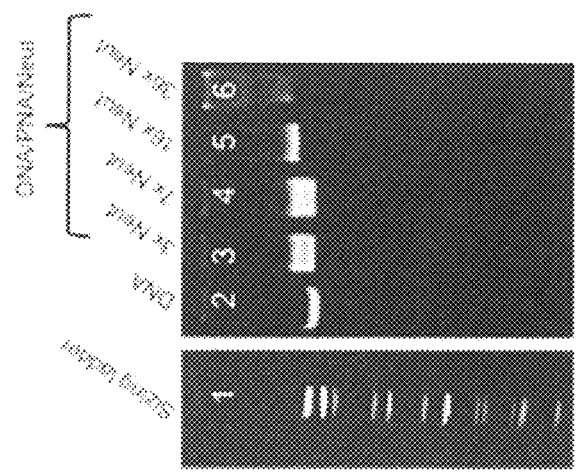
FIG. 12c shows the effect of neutravidin on the migration speed of DNA in a gel shift assay.

FIGS. 12a-b show data comparing $\Delta I$ vs. $t_D$ distributions from three separate experiments: DNA alone, Neutravidin alone, and D/P/N reagents. The largest |$\Delta I$| events in the D/P/N experiment are attributed to D/P/N complexes (FIG. 11d), providing a simple criteria for tagging events based on their binding state (i.e., unbound, scaffold with PNA, and scaffold with PNA and Neutravidin bound). Specifically, we flagged an event as being "capture-molecule bound" (i.e., D/P/N complex) if |$\Delta I$|>4 nA for that event. For the data sets in FIG. 12a, 9.3% (390) of events in the D/P/N experiment have |$\Delta I$|>4 nA, with only 0.46% of D and 0.16% of N events in controls exceeding 4 nA. In a separate experiment (data not shown) we used a 7 nm diameter pore at 1 M KCl and 200 mV applied. We ran a control with only PNA and Neutravidin at 0.4 nM concentration. No events (0%) exceeded 4 nA. Applying our mathematical criteria, the random variable Q={Fraction of flagged events} had a binomial distribution, and using this and other statistical modeling tools, we computed the 99% confidence interval for this data set as Q=9.29±1.15%. Since 9.29%>0.46% (the max false-positive %) is satisfied well within the 99% confidence interval for Q, we have a positive test result, and in under 8 minutes of data gathering. In fact the same 99% confidence was achieved for this data set with only the first 60 seconds of the data. The gel shift (FIG. 12c) shows that scaffold DNA migration was retarded in a Neutravidin dependent manner. Thus, we used the 10× concentration in this experiment, as it appeared all DNA is labeled and a nearly homogenous population was created.

Labeling a DNA scaffold with PNA-Biotin for the capture of neutravidin is similar in reagent size only, and thus used to confirm a nanopore of particular size is able to detect this molecule. The nature of the biotin-neutravidin interaction is very different from the boronic acid-diol reaction that this proposal outlines. Namely, biotin does not chemically react with neutravidin, but instead binding is from Hydrogen bonds and van der Waals forces. Boronic acid chemically reacts with diol to form stable covalent bounds. Additionally, biotin is only able to bind to avidin and avidin derivatives, whereas boronic acid is selective for cis-diols.

Therefore, we have shown that detection of representative capture molecules on scaffolds can be demonstrated, and further that detection of target molecules to capture molecules on the scaffold can also be detected. With this capability, discrimination is achieved by engineering the ligand domain of the capture molecule to achieve specificity of detection in the nanopore for the target molecule of interest.

Example 3—Capture Molecules Comprising PNA Linked to Boronic Acid Moieties

Figure 13A:
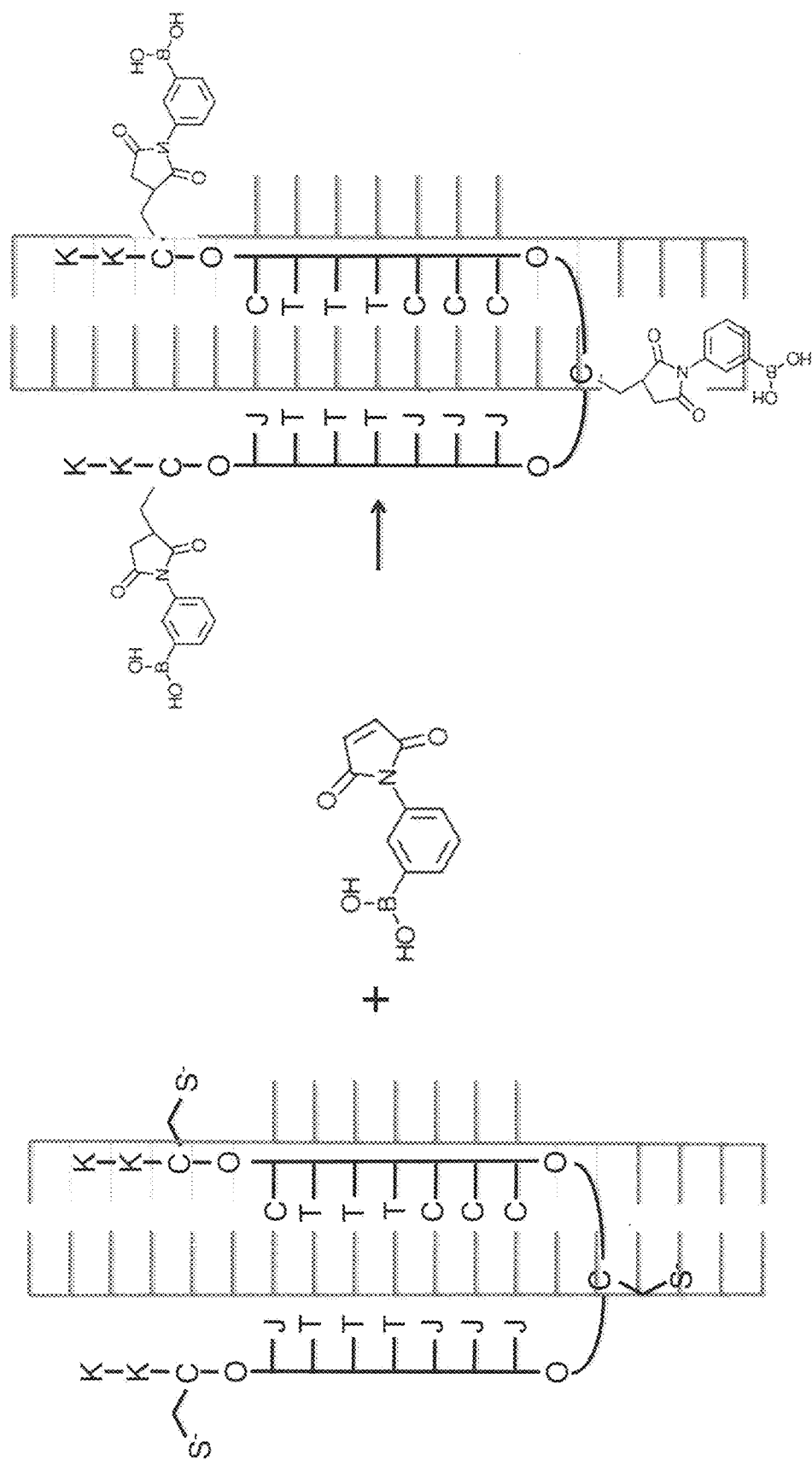
FIG. 13a shows the structure of a bisPNA binding to a DNA scaffold.
Figures 13B, 13C:
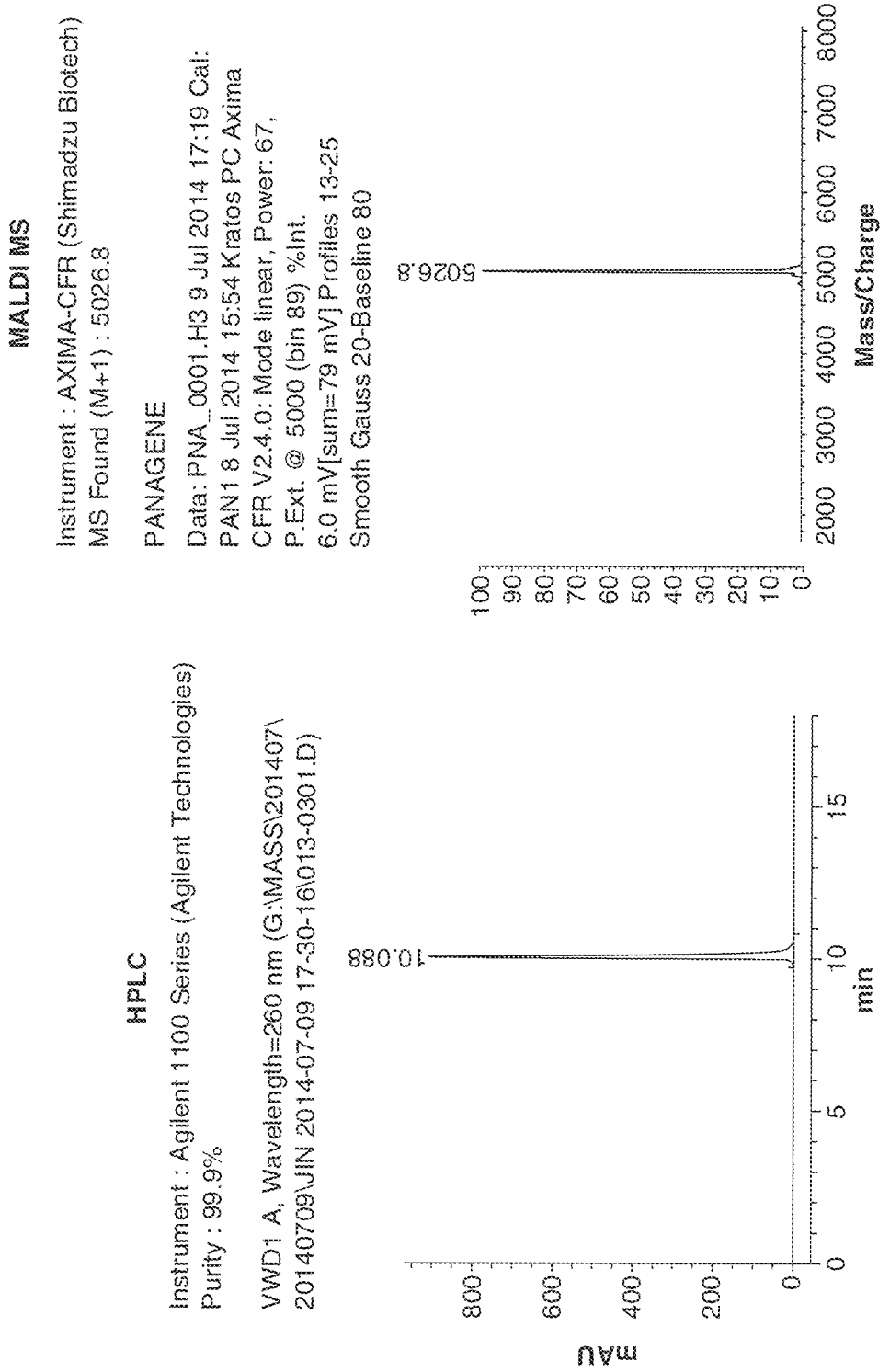
FIG. 13b and FIG.c show confirmation of creation of this molecule with HPLC and MALDI MS.

FIG. 13a shows the structure of a bisPNA bound to a DNA scaffold. The PNA contained three cysteines in the backbone and in PEG linkers to provide accurate base spacing and hinge region flexibility. The creation of the PEG molecule was verified by HPLC purification and Mass Spectrometry, FIG. 13b,c.

Figure 14A:
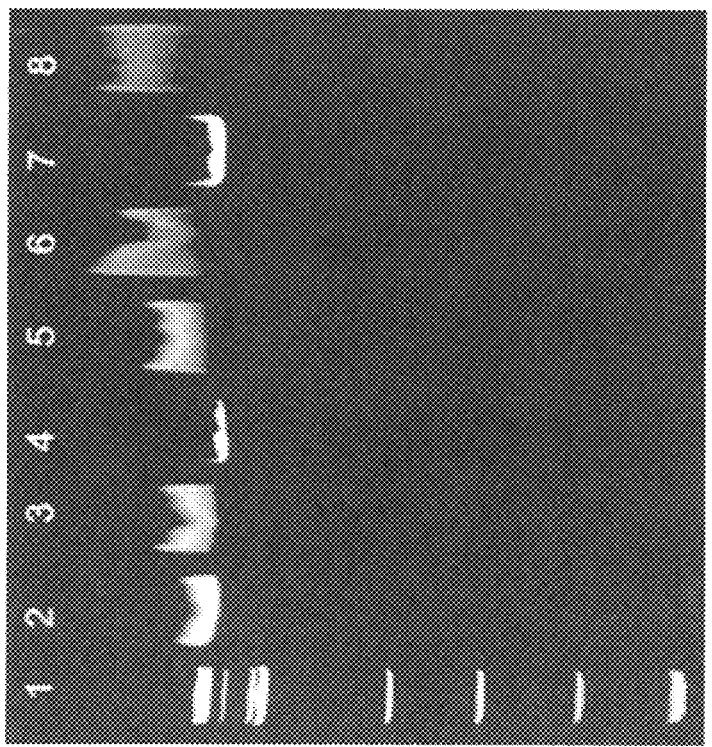
FIG. 14a is a gel shift assay showing binding of bisPNA to DNA.

To create DNA/bisPNA-boronic acid reagent for detecting diol-containing biomarkers, the following protocol was used:

bisPNA (FIG. 13a) was resuspended in 10 mM sodium phosphate (NaPi) buffer (pH 7.0) to a final concentration of 50 µM. A 1 mM solution of MTSEA (2-Aminoethyl methanethiosulfonate hydrobromide) was added to the bisPNA suspension and allowed to react for 1 hour at 37° C. to create the PNA-MTSEA compound. FIG. 14a shows a gel shift assay using this PNA molecule, demonstrating it bound to DNA. Increasing the PNA concentration gave greater shift since additional sites were occupied. Free thiols on the bis-PNA were capped to prevent cysteine or disulfide oxidation.

The solution of 50 µM bis-PNA MTSEA was then incubated with 1 µM scaffold (containing target sites for PNA binding) at 42° C. for 24 hours in 50 mM NaCl, 10 mM NaPi, and 1 mM EDTA (at pH 7.0). PNA-MTSEA-Scaffold complexes were then isolated using a 40 k MWCO spin column (Zeba Micro Spin Desalting Columns, Piercenet).

1 mM TCEP (pH 6.5) and 10 mM NaPi was then added to the isolated bisPNA-MTSEA-DNA complexes and allowed to react at 37° C. for 1 hour to reduce the mixed disulfides and to free thiols.

A bis-maleimide linker (1,11-bismaleimidotriethyleneglycol, Piercenet) was resuspended to 5 mM in 10 mM NaPi (pH 6.5), and then allowed to react with 1 µM DNA-bisPNA at room temperature for 15 minutes. The DNA-bisPNA-linker was then purified from the solution using a Zeba micro-spin column.

1 mM thiol-phenyl-boronic acid was then added to the DNA-bisPNA-linker complex and allowed to react for 1 hour at room temperature. The DNA-bisPNA-linker-boronic acid complex was then isolated using a micro-spin column. This complex was the final reagent for detection in a nanopore.

Figure 14B:
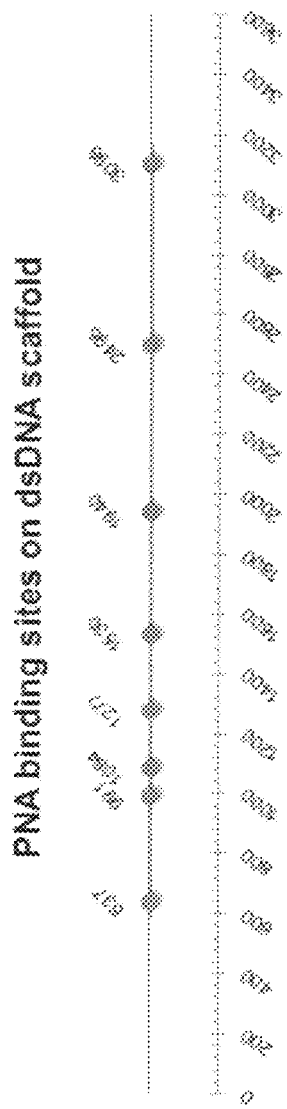
FIG. 14b is a schematic diagram of PNA binding sites on the dsDNA scaffold.

FIG. 14b shows the 8 PNA binding sites on this dsDNA scaffold used in this experiment.

It is to be understood that while the invention has been described in conjunction with the above embodiments, the foregoing description and examples are intended to illustrate and not limit the scope of the invention. Other aspects, advantages and modifications within the scope of the invention will be apparent to those skilled in the art to which the invention pertains.

The invention claimed is:

1. A method for detecting the presence or absence of a diol in a sample, comprising:
   contacting the sample with a plurality of probes, wherein each of the probes is covalently linked to a reactive organoboronic moiety capable of specifically binding to a different diol under a condition for the diol to bind to the reactive organoboronic moiety, and wherein each of the probes can specifically recognize and bind to a binding site on a charged polymeric scaffold, wherein the charged polymeric scaffold comprises a plurality of binding sites, wherein each of the binding sites is specific for each of the probes;
   loading the sample contacted with the plurality probes, and the charged polymeric scaffold to a device under the condition, wherein the device comprises (i) a pore located between two volumes of an interior space of said device, and (ii) a sensor configured to identify an object passing through the pore;
   inducing passage of the charged polymeric scaffold through the pore from one volume to the other volume of the device by applying a voltage across the pore; and
   determining with the sensor whether the probe bound to the charged polymeric scaffold is further bound to the diol, thereby determining the presence or absence of the diol in the sample.

2. A method for detecting the presence or absence of a diol in a sample, comprising:
   contacting the sample with a probe, wherein said probe comprises a polynucleotide and is covalently linked to one or more reactive organoboronic moiety that is capable of specifically binding to the diol under a condition for the diol to bind to the reactive organoboronic moiety, and wherein the probe can specifically recognize and bind to a binding site on a charged polymeric scaffold;
   loading the sample contacted with the probe, and the charged polymeric scaffold to a device under the condition, wherein the device comprises (i) a pore located between two volumes of an interior space of said device, and (ii) a sensor configured to identify an object passing through the pore;
   inducing passage of the charged polymeric scaffold through the pore from one volume to the other volume of the device by applying a voltage across the pore; and
   determining with the sensor whether the probe bound to the charged polymeric scaffold is further bound to the diol, thereby determining the presence or absence of the diol in the sample.

3. The method of claim 2, wherein said polynucleotide comprises a ribonucleic acid, a deoxyribonucleic acid, or a peptide nucleic acid.

4. The method of claim 2, wherein the binding site on the charged polymeric scaffold has sequence complementarity with said probe.

5. The method of claim 2, wherein the polynucleotide is not longer than 100 bases in length.

6. The method of claim 2, wherein the organoboronic moiety is covalently linked to the backbone of the polynucleotide.

7. The method of claim 2, wherein the organoboronic moiety is covalently linked to a base of the polynucleotide.

8. A method for detecting the presence or absence of a diol in a sample, comprising:
   contacting the sample with a probe, wherein the probe is bound to a linker comprising an amino acid, the linker is bound to a reactive organoboronic moiety, and the reactive organoboronic moiety is capable of specifically binding to the diol under a condition for the diol to bind to the reactive organoboronic moiety, and wherein the probe can specifically recognize and bind to a binding site on a charged polymeric scaffold;
   loading the sample contacted with the probe, and the charged polymeric scaffold to a device under the condition, wherein the device comprises (i) a pore located between two volumes of an interior space of said device, and (ii) a sensor configured to identify an object passing through the pore;
   inducing passage of the charged polymeric scaffold through the pore from one volume to the other volume of the device by applying a voltage across the pore; and
   determining with the sensor whether the probe bound to the charged polymeric scaffold is further bound to the diol, thereby determining the presence or absence of the diol in the sample.

9. A method for detecting the presence or absence of a diol in a sample, comprising:
   contacting the sample with a probe, wherein the probe is bound to a linker, the linker is bound to a reactive organoboronic moiety, and the reactive organoboronic moiety is capable of specifically binding to the diol under a condition for the diol to bind to the reactive organoboronic moiety, wherein the probe can specifically recognize and bind to a binding site on a charged polymeric scaffold, and wherein the linker is selected from a group consisting of:

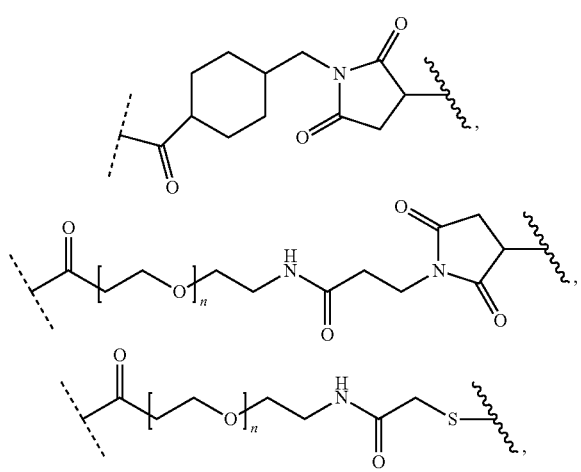

-continued

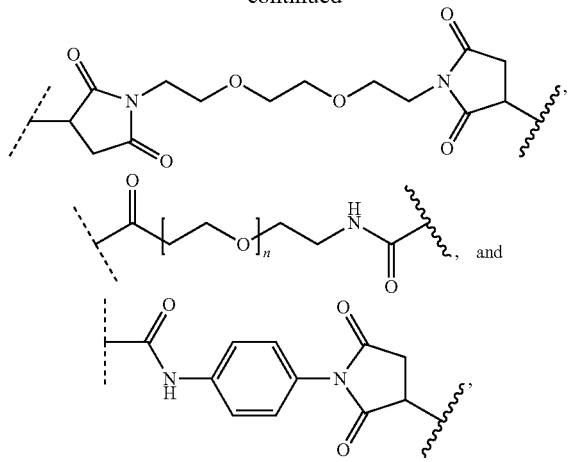

wherein ----- represents the point of connection or linkage of the reactive organoboronic moiety to the linker and, ∿∿∿ represents the point of connection or linkage to the probe;

loading the sample contacted with the probe, and the charged polymeric scaffold to a device under the condition, wherein the device comprises (i) a pore located between two volumes of an interior space of said device, and (ii) a sensor configured to identify an object passing through the pore;

inducing passage of the charged polymeric scaffold through the pore from one volume to the other volume of the device by applying a voltage across the pore; and determining with the sensor whether the probe bound to the charged polymeric scaffold is further bound to the diol, thereby determining the presence or absence of the diol in the sample.

10. A method for detecting the presence or absence of a diol in a sample, comprising:

contacting the sample with a probe, wherein the probe is covalently linked to one or more reactive organoboronic moiety that is capable of specifically binding to the diol under a condition for the diol to bind to the reactive organoboronic moiety, and wherein the probe can specifically recognize and bind to a binding site on a charged polymeric scaffold, wherein said charged polymeric scaffold comprises a polynucleotide;

loading the sample contacted with the probe, and the charged polymeric scaffold to a device under the condition, wherein the device comprises (i) a pore located between two volumes of an interior space of said device, and (ii) a sensor configured to identify an object passing through the pore;

inducing passage of the charged polymeric scaffold through the pore from one volume to the other volume of the device by applying a voltage across the pore; and determining with the sensor whether the probe bound to the charged polymeric scaffold is further bound to the diol, thereby determining the presence or absence of the diol in the sample.

11. The method of 10, wherein the charged polymeric scaffold is a single-stranded or double-stranded polynucleotide.

12. The method of claim 10, wherein the charged polymeric scaffold is a polynucleotide of at least 100 bases in length.

13. The method of claim 10, wherein the binding site on the charged polymeric scaffold comprises at least 2, 3, 4, 5, 6, 7, 8, 9, 10, 11, 12, 13, 14, 15, 16, 17, 18, 19, or 20 consecutive bases.

14. A method for detecting the presence or absence of a first and second diol in a sample, comprising:

contacting the sample with a first probe, wherein the first probe is covalently linked to a first organoboronic moiety that is capable of specifically binding to a first diol under a condition, and wherein the first probe can specifically recognize and bind to a first binding site on a charged polymeric scaffold;

contacting the sample with a second probe, wherein the second probe is covalently linked to a second organoboronic moiety capable of binding to a second diol under the condition, wherein the second probe can specifically recognize and bind to a second binding site on the charged polymeric scaffold, wherein said first and second diol are different, and wherein said first and second organoboronic moieties are different;

loading the sample contacted with the first probe and the second probe, and the charged polymeric scaffold to a device under the condition, wherein the device comprises (i) a pore located between two volumes of an interior space of said device, and (ii) a sensor configured to identify an object passing through the pore;

inducing passage of the charged polymeric scaffold through the pore from one volume to the other volume of the device by applying a voltage across the pore; and determining with the sensor whether the first probe bound to the charged polymeric scaffold is further bound to the first diol, and whether the second probe bound to the charged polymeric scaffold is further bound to the second diol, thereby determining the presence or absence of the first and second diol in the sample.

15. The method of claim 14, wherein said first probe comprises a region complementary to a first sequence on the charged polymeric scaffold, and wherein said second probe comprises a region complementary to a second sequence on the charged polymeric scaffold, wherein said first and second sequence are different.

\* \* \* \* \*

UNITED STATES PATENT AND TRADEMARK OFFICE
CERTIFICATE OF CORRECTION

PATENT NO. : 10,597,702 B2  
APPLICATION NO. : 14/912884  
DATED : March 24, 2020  
INVENTOR(S) : Trevor J. Morin Page 1 of 1

It is certified that error appears in the above-identified patent and that said Letters Patent is hereby corrected as shown below:

In the Claims

In Column 31, in Claim 1, Line 23, after "plurality" insert -- of --

In Column 33, in Claim 9, Line 22, delete "and," and insert -- and --

In Column 34, in Claim 11, Line 8, delete "of 10," and insert -- of claim 10, --

Signed and Sealed this
Twenty-ninth Day of September, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
```

```
         oligonucleotide

<400> SEQUENCE: 1
gaaagtgaaa gt                                                        12
```